(12) United States Patent
Oshima

(10) Patent No.: US 9,138,417 B2
(45) Date of Patent: *Sep. 22, 2015

(54) CONTROLLED RELEASE PARTICLES AND PRODUCTION METHOD THEREOF

(75) Inventor: Junji Oshima, Osaka (JP)

(73) Assignee: OSAKA GAS CHEMICALS CO., LTD., Osaka-shi (JP)

(*) Notice: Subject to any disclaimer, the term of this patent is extended or adjusted under 35 U.S.C. 154(b) by 0 days.

This patent is subject to a terminal disclaimer.

(21) Appl. No.: 14/003,265

(22) PCT Filed: Mar. 8, 2012

(86) PCT No.: PCT/JP2012/055969
§ 371 (c)(1),
(2), (4) Date: Sep. 5, 2013

(87) PCT Pub. No.: WO2012/124599
PCT Pub. Date: Sep. 20, 2012

(65) Prior Publication Data
US 2013/0337072 A1    Dec. 19, 2013

(30) Foreign Application Priority Data

Mar. 11, 2011  (JP) ................................. 2011-054627
Feb. 23, 2012  (JP) ................................. 2012-037886

(51) Int. Cl.
*A61K 9/50*   (2006.01)
*A01N 25/28*  (2006.01)

(52) U.S. Cl.
CPC .............. *A61K 9/5026* (2013.01); *A01N 25/28* (2013.01)

(58) Field of Classification Search
None
See application file for complete search history.

(56) References Cited

U.S. PATENT DOCUMENTS 3,832,252 A * 8/1974 Higuchi et al.
5,169,632 A * 12/1992 Duell et al. ................... 424/408

(Continued)

FOREIGN PATENT DOCUMENTS

| CA | 2 385 991 A1 | 4/2001 |
|----|--------------|--------|
| CN | 101132851 A  | 2/2008 |

(Continued)

OTHER PUBLICATIONS

International Search Report (PCT/ISA/210) mailed on Jun. 12, 2012 by the Japanese Patent Office as the International Searching Authority for International Application No. PCT/JP2012/055969.

(Continued)

*Primary Examiner* — Robert A Wax
*Assistant Examiner* — Milissa Mercier
(74) *Attorney, Agent, or Firm* — Buchanan, Ingersoll & Rooney PC

(57) ABSTRACT

A controlled release particle includes a core containing an antibiotic compound, and a shell covering the core. The controlled release particle is obtained by a production method including a first step in which a first component containing an antibiotic compound and a polymerizable vinyl monomer is subjected to suspension polymerization to form the core containing the antibiotic compound and a polymer of the polymerizable vinyl monomer; and a second step in which a second component containing a shell-forming component is subjected to interfacial polymerization to form a shell, wherein in the second step, the interfacial polymerization is started simultaneously with the start of the suspension polymerization of the first step, or started after the start of the suspension polymerization of the first step.

2 Claims, 13 Drawing Sheets

SEM Photograph of Example 1

(56) References Cited

U.S. PATENT DOCUMENTS

| | | | |
|---|---|---|---|
| 6,471,975 | B1 | 10/2002 | Banovetz et al. |
| 8,808,752 | B2 * | 8/2014 | Oshima ........................ 424/501 |
| 2008/0207445 | A1 | 8/2008 | Dexter et al. |
| 2009/0130156 | A1 | 5/2009 | Borzatta et al. |

FOREIGN PATENT DOCUMENTS

| | | |
|---|---|---|
| CN | 101163401 A | 4/2008 |
| JP | 61-033230 A | 2/1986 |
| JP | 62-061901 | 3/1987 |
| JP | 63-137746 A | 6/1988 |
| JP | 6-312128 A | 11/1994 |
| JP | 11-505464 A | 5/1999 |
| JP | 2001-139870 A | 5/2001 |
| JP | 2001-247409 | 9/2001 |
| JP | 2002-513038 A | 5/2002 |
| JP | 2003-517464 A | 5/2003 |
| WO | WO 96/03039 A1 | 2/1996 |
| WO | WO 99/56541 | 11/1999 |
| WO | WO 2006/092409 A2 | 9/2006 |
| WO | WO 2006/111553 A1 | 10/2006 |

OTHER PUBLICATIONS

Written Opinion (PCT/ISA/237) mailed on Jun. 12, 2012 by the Japanese Patent Office as the International Searching Authority for International Application No. PCT/JP2012/055969.

Notification Concerning Transmittal of Copy of International Preliminary Report on Patentability and Written Opinion (PCT/ISA/326, PCT/ISA/373 and PCT/ISA/237) mailed on Sep. 26, 2013 issued in corresponding International Application No. PCT/JP2012/055969.

Notification of Transmittal of Copies of Translation of the International Preliminary Report on Patentability International Application No. PCT/JP2012/055969.

* cited by examiner

SEM Photograph of Example 1

SEM Photograph of Example 2

SEM Photograph of Example 3

SEM Photograph of Example 4

SEM Photograph of Example 5

SEM Photograph of Example 6

SEM Photograph of Example 7

SEM Photograph of Example 8

SEM Photograph of Comparative Example 1

SEM Photograph of Comparative Example 2

SEM Photograph of Comparative Example 4

TEM Photograph of Example 2

FIG.13 TEM Photograph of Example 3
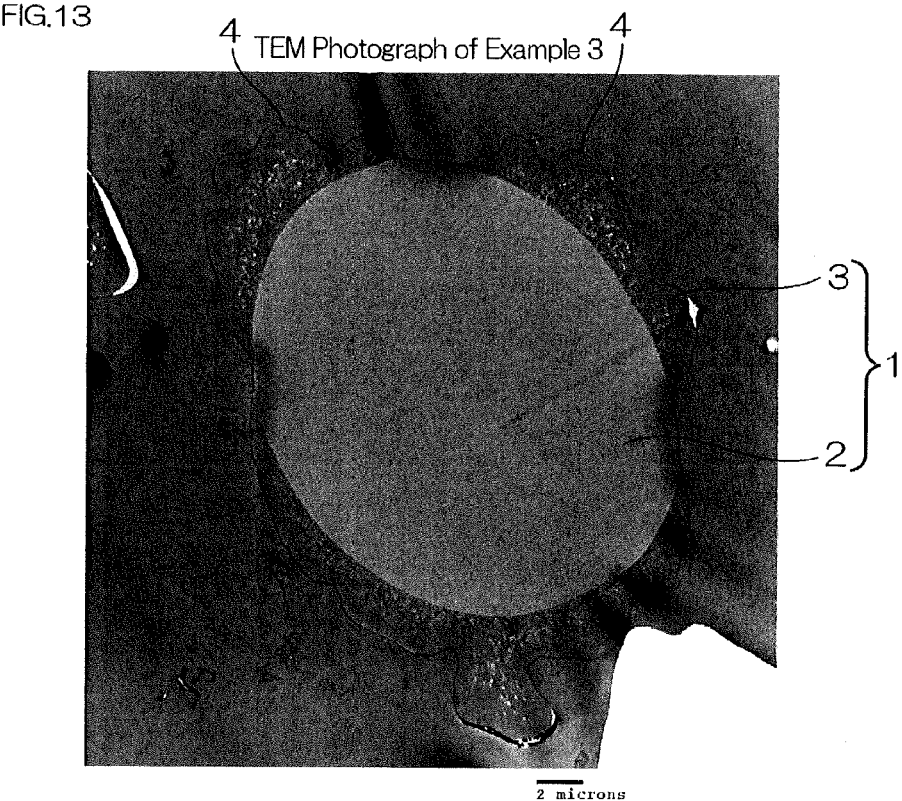
FIG.14 TEM Photograph of Example 5
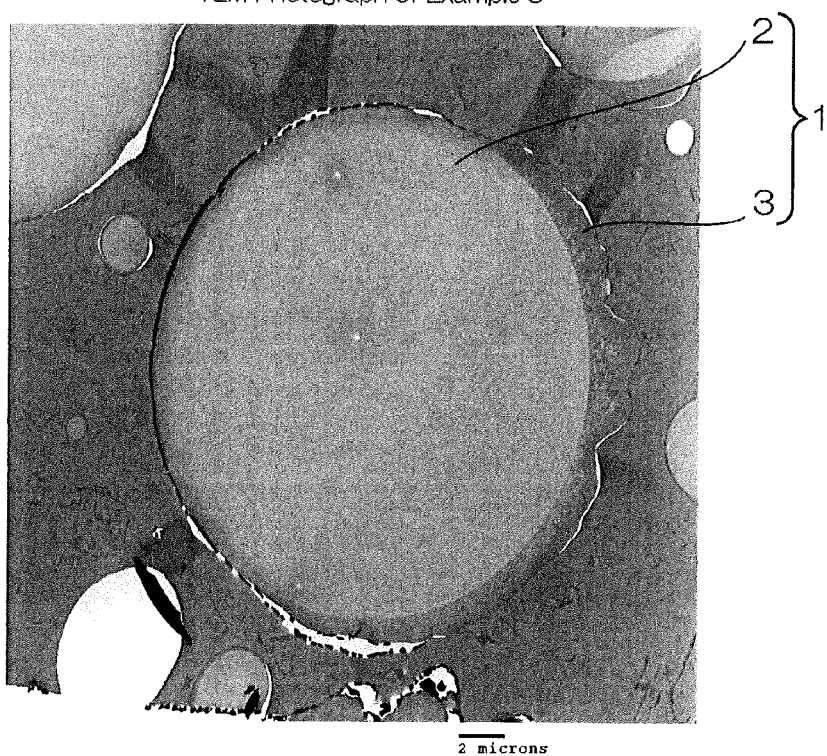

TEM Photograph of Comparative Example 1

TEM Photograph of Comparative Example 2

CONTROLLED RELEASE PARTICLES AND PRODUCTION METHOD THEREOF

TECHNICAL FIELD

The present invention relates to controlled release particles and a method for producing the same, in particular, to controlled release particles that allow controlled-release of an antibiotic compound and to a method for producing the same.

BACKGROUND ART

It is known that micro-encapsulation of antibiotic compounds such as a sterilizer, an antiseptic, and a fungicide allow controlled-release of the antibiotic compound to ensure lasting effects.

For example, a microbial growth inhibitor-containing microcapsule (for example, see Patent Document 1 below) has been proposed: the microbial growth inhibitor-containing microcapsule is obtained by blending and dispersing an oil phase including a microbial growth inhibitor and a polyisocyanate component, and an aqueous phase including an active hydrogen group-containing component, and allowing interfacial polymerization.

CITATION LIST

Patent Document

Patent Document 1: Japanese Unexamined Patent Publication No. 2001-247409

SUMMARY OF THE INVENTION

Problem to be Solved by the Invention

However, there are disadvantages in the above-described Patent Document 1 in that the microbial growth inhibitor-containing microcapsule described in Patent Document 1 has insufficient controlled release properties.

An object of the present invention is to provide controlled release particles excellent in controlled release properties, and a production method thereof.

Means for Solving the Problem

The present inventors made an energetic study on the controlled release particles and a production method thereof of the above object, and found out that a shell allows reliable covering of a core containing an antibiotic compound and a polymer, and as a result of further advancing the study, accomplished the present invention.

That is, the present invention relates to the following.
(1) A controlled release particle including a core containing an antibiotic compound and a shell covering the core,
wherein the controlled release particle is obtained by a production method including
a first step in which a first component containing the antibiotic compound and a polymerizable vinyl monomer is subjected to suspension polymerization to form the core containing the antibiotic compound and a polymer of the polymerizable vinyl monomer, and
a second step in which a second component containing a shell-forming component is subjected to interfacial polymerization to form the shell,
wherein in the second step, the interfacial polymerization is started simultaneously with the start of the suspension polymerization of the first step, or started after the start of the suspension polymerization of the first step;
(2) The controlled release particle of the above (1),
wherein the antibiotic compound has a polar term $\delta_{p,compound}$ of 2 to 8 $[(J/cm^3)^{1/2}]$ and a hydrogen bonding term $\delta_{h,compound}$ of 5.5 to 9.5 $[(J/cm^3)^{1/2}]$ of a solubility parameter $\delta$ and the polymer has a polar term $\delta_{p,polymer}$ of 5 to 7 $[(J/cm^3)^{1/2}]$ and a hydrogen bonding term $\delta_{h,polymer}$ of 8 to 10 $[(J/cm^3)^{1/2}]$ of the solubility parameter $\delta$ the solubility parameter $\delta$ being defined by Hansen and calculated by van Krevelen and Hoftyzer method; and
(3) A method for producing a controlled release particle, the method including
a first step in which a first component containing an antibiotic compound and a polymerizable vinyl monomer is subjected to suspension polymerization to form a core containing the antibiotic compound and a polymer of the polymerizable vinyl monomer, and
a second step in which a second component containing a shell-forming component is subjected to interfacial polymerization to form a shell covering the core,
wherein in the second step, the interfacial polymerization is started simultaneously with the start of the suspension polymerization of the first step, or started after the start of the suspension polymerization of the first step.

Effect of the Invention

In the method for producing a controlled release particle of the present invention, in the second step, the interfacial polymerization is started at the same time with the start of the suspension polymerization of the first step, or started after the start of the suspension polymerization of the first step, and therefore the shell can reliably cover the core containing the antibiotic compound and the polymer.

Therefore, by suppressing the releasing speed of the antibiotic compound, the controlled release particle of the present invention having excellent controlled release properties, and capable of exhibiting excellent lasting effects can be obtained.

BRIEF DESCRIPTION OF THE DRAWINGS

FIG. 13 shows an image-processed TEM photograph of controlled release particles of Example 3.

FIG. 14 shows an image-processed TEM photograph of controlled release particles of Example 5.

EMBODIMENT OF THE INVENTION

A controlled release particle of the present invention includes a core containing an antibiotic compound, and a shell covering the core.

The core is formed into a generally spherical form.

Figure 12:
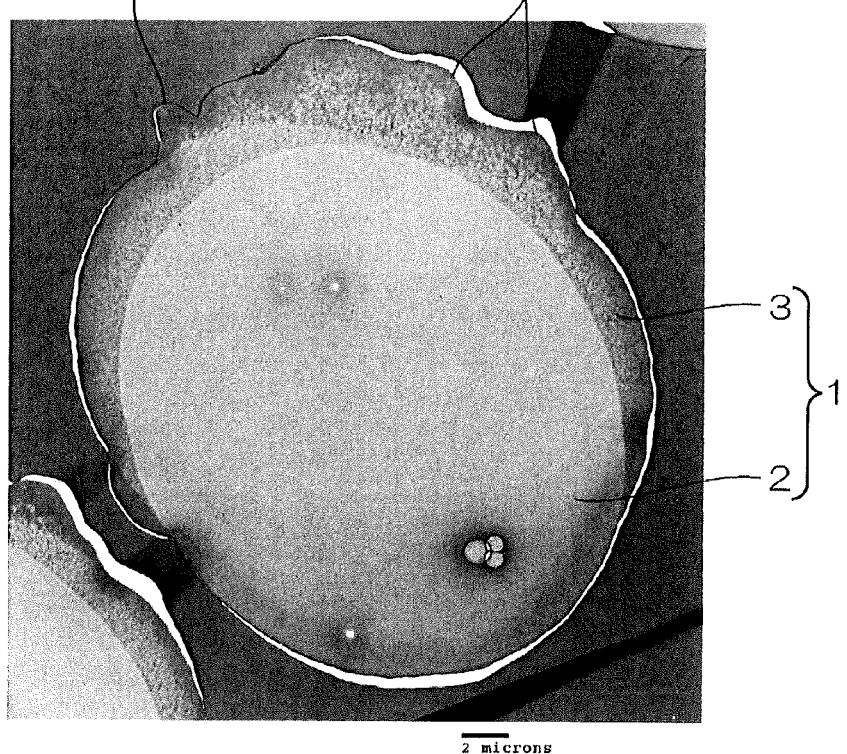
FIG. 12 shows an image-processed TEM photograph of controlled release particles of Example 2.

The shell is formed into a film that covers the surface of the core. As shown in TEM photographs of FIG. 12 to FIG. 14, the shell (3) is formed along the periphery of the core (2) so that the shell (3) has a non-uniform thickness. As shown in FIG. 12, the shell (3) has a comparatively smooth surface, or, as shown in FIG. 13 and FIG. 14, the shell (3) has a comparatively rough surface relative to that of FIG. 12.

The controlled release particle of the present invention can be obtained by a production method including a first step in which a first component containing an antibiotic compound and a polymerizable vinyl monomer is subjected to suspension polymerization to form a core containing an antibiotic compound and a polymer of the polymerizable vinyl monomer; and a second step in which a second component containing a shell-forming component is subjected to interfacial polymerization to form a shell.

The antibiotic compound has, for example, at least two functional moieties that are capable of interacting with the polymer of the polymerizable vinyl monomer.

Examples of such functional moieties include polar functional groups such as a carbonyl group, a nitro group, an amino group, a cyano group, a phosphate group, a carboxyl group, and an ether group; polar bonds containing a polar group such as a carboxylate bond, a phosphate bond, a urea bond, and a carbon-halogen bond; and conjugated cyclic portions such as a benzene ring, and further a conjugated heterocyclic ring such as a triazine ring, an imidazole ring, and an isothiazoline ring.

The antibiotic compound has a molecular weight of, for example, 200 to 600, preferably 200 to 500.

When the antibiotic compound has a molecular weight exceeding the above-described range, miscibility of the antibiotic compound with the polymer may be reduced. On the other hand, when the antibiotic compound has a molecular weight below the above-described range, there is a case where the antibiotic compound remains in the aqueous phase during suspension polymerization, and after the suspension polymerization, the antibiotic compound separates out, solidifying the suspension liquid.

The antibiotic compound has a melting point of, for example, 100° C. or less, preferably 90° C. or less, and more preferably 80° C. or less. When the antibiotic compound has a melting point exceeding the above-described range, there may be a case where the antibiotic compound is not easily encapsulated in the core and separates outside the core, and even if the antibiotic compound is encapsulated in the core, controlled-release of the antibiotic compound to the outside the core may not be allowed.

To be specific, the antibiotic compound is selected from a sterilizer, an antibacterial agent, an antiseptic, an antialgae, a fungicide, an insecticide, a herbicide, an attractant, a repellent, a rodenticide, etc. having antibiotic activities such as, for example, sterilizing, antibacterial, antiseptic, antialgae, antifungal, and insecticidal activity. Examples of these compounds having antibiotic activity include sterilizing antiseptic antialgae fungicides such as an iodine compound, a triazole compound, a carbamoyl imidazole compound, a dithiol compound, an isothiazoline compound, a nitro alcohol compound, and p-hydroxybenzoate ester; and termite control agents (termite killers) such as a pyrethroid compound, a neonicotinoid compound, an organic chlorine compound, an organic phosphorus compound, a carbamate compound, an alkoxyamine compound, and an oxadiazon compound.

Examples of iodine compounds include 3-iodo-2-propynylbutylcarbamate (IPBC), 1-[[(3-iodo-2-propynyl)oxy]methoxy]-4-methoxybenzene, and 3-bromo-2,3-diiodo-2-propenyl ethyl carbonate.

Examples of triazole compounds include 1-[2-(2,4-dichlorophenyl)-4-n-propyl-1,3-dioxolane-2-ylmethyl]-1H-1,2,4-triazole (propiconazole), and bis(4-fluorophenyl)methyl(1H-1,2,4-triazole-1-ylmethylsilane) (also called: flusilazole, 1-[[bis(4-fluorophenyl)methylsilyl]methyl]-1H-1,2,4-triazole).

Examples of carbamoyl imidazole compounds include N-propyl-N-[2-(2,4,6-trichloro-phenoxy)ethyl]imidazole-1-carboxamide (prochloraz).

Examples of dithiol compounds include 4,5-dichloro-1,2-dithiol-3-one.

Examples of isothiazoline compounds include 2-n-octyl-4-isothiazoline-3-one (OIT), 5,6-dichloro-2-n-octyl-4-isothiazoline-3-one (DCOIT), and 5-chloro-2-methyl-4-isothiazoline-3-one (Cl-MIT).

Examples of nitro alcohol compounds include 2,2-dibromo-2-nitro-1-ethanol (DBNE).

Examples of p-hydroxybenzoate esters include butyl p-hydroxybenzoate and propyl p-hydroxybenzoate.

Examples of pyrethroid compounds include pyrethrin obtained from pyrethrum, cinerin, and jasmoline; and also include allethrin, bifenthrin, acrinathrin, α-cypermethrin, tralomethrin, cyfluthrin (RS)-α-cvano-4-fluoro-3-phenoxybenzyl-(1RS,3RS)-(1RS,3RS)-3-(2,2-dichlorovinyl)-2,2-dimethylcyclopropane carboxylate), cyphenothrin, prallethrin, ethofenprox, silafluofen, and fenvalerate derived therefrom.

Examples of neonicotinoid compounds include (E)-$N^1$-[(6-chloro-3-pyridyl)methyl]-$N^2$-cyano-$N^1$-methylacetamidine (acetamiprid).

Examples of organic chlorine compounds include Kelthane.

Examples of organic phosphorus compounds include phoxim, pyridaphenthion, fenitrothion, tetrachlorvinphos, dichlofenthion, and propetamphos.

Examples of carbamate compounds include fenobucarb and propoxur.

Examples of alkoxyamine compound include 3-lauryloxypropylamine.

Examples of oxadiazon compounds include indoxacarb.

Examples of insecticides include pyriproxyfen.

Examples of herbicides include pyraclonil, pendimethalin, and indanofan.

Examples of repellents include Deet.

The antibiotic compound is substantially hydrophobic, and, to be specific, has a quite low water solubility at room temperature (20 to 30° C., to be more specific, 25° C.), to more be specific, for example, a solubility at room temperature of, on a mass basis, 1 part by mass/100 parts by mass of water (10000 ppm) or less, preferably 0.5 parts by mass/100 parts by mass of water (5000 ppm) or less, and more preferably 0.1 parts by mass/100 parts by mass of water (1000 ppm) or less; and on a volume basis, for example, 1 g/100 mL of water or less, preferably 0.5 g/100 mL of water or less, and more preferably 0.1 g/100 mL of water or less.

When the antibiotic compound has a water solubility exceeding the above-described range, at the time of suspension polymerization of the first component containing a polymerizable vinyl monomer, the antibiotic compound easily leaks out to the outside (that is, aqueous phase) of the core, and after the polymerization, the antibiotic compound dissolved in the aqueous phase separates out, and therefore formation of the core containing the antibiotic compound may become difficult.

These antibiotic compounds can be used alone or in combination of two or more.

The above-described antibiotic compound may contain, for example, in the production processes, impurities having a melting point of outside the above-described range at an appropriate proportion. To be specific, a mixture of isomer 1 (melting point: 57° C.), isomer II (melting point: 74° C.), and isomer III (melting point: 66° C.) of cyfluthrin contains, for example, an impurity of isomer IV (melting point 102° C.).

The polymerizable vinyl monomer is, for example, a monomer having at least one polymerizable carbon-carbon double bond in its molecule.

To be specific, examples of the polymerizable vinyl monomer include a (meth)acrylate monomer, a (meth)acrylic acid monomer, an aromatic vinyl monomer, a vinyl ester monomer, a maleate monomer, a vinyl halide monomer, and a nitrogen-containing vinyl monomer.

Examples of (meth)acrylate monomers include methacrylates and/or acrylates, to be specific, methyl (meth)acrylate, ethyl (meth)acrylate, n-propyl (meth)acrylate, iso-propyl (meth)acrylate, n-butyl (meth)acrylate, iso-butyl (meth)acrylate, tert-butyl (meth)acrylate, cyclohexyl (meth)acrylate, and 2-methoxyethyl (meth)acrylate.

Examples of (meth)acrylic acid monomer include methacrylic acid and acrylic acid.

Examples of aromatic vinyl monomers include styrene, chlorostyrene, p-methyl styrene, o-methyl styrene, and α-methyl styrene.

Examples of vinyl ester monomers include vinyl acetate and vinyl propionate.

Examples of maleate monomers include dimethyl maleate, diethyl maleate, and dibutyl maleate.

Examples of vinyl halide monomers include vinyl chloride and vinyl fluoride. Examples of vinyl halide monomer also include vinylidene halide monomers, to be specific, vinylidene chloride and vinylidene fluoride.

Examples of nitrogen-containing vinyl monomers include (meth)acrylonitrile, N-phenylmaleimide, and vinylpyridine.

The polymerizable vinyl monomer is substantially hydrophobic, and to be specific, has a significantly low water solubility at room temperature, to be more specific, a solubility at room temperature of, for example, 10 parts by mass/100 parts by mass of water or less, preferably 8 parts by mass/100 parts by mass of water or less.

Of the above-described polymerizable vinyl monomers, for example, an antibiotic compound-miscible monomer (hereinafter sometimes simply referred to as a miscible monomer) that is highly miscible with the above-described antibiotic compound and is capable of dissolving (being miscible with) the antibiotic compound is selected.

These miscible monomers can be used alone or in combination of two or more.

As the miscible monomer, preferably, a (meth)acrylate monomer is used alone, or a (meth)acrylate monomer is used with a (meth)acrylic acid monomer in combination.

To be specific, methyl methacrylate (MMA) is used alone, or used in combination with methyl methacrylate and methacrylic acid.

When a (meth)acrylate monomer and a (meth)acrylic acid monomer are used in combination, the mixing ratio of the (meth)acrylic acid monomer relative to 100 parts by mass of the miscible monomer is, for example, below 30 parts by mass, preferably 20 parts by mass or less, and, for example, 1 part by mass or more, preferably 3 parts by mass or more.

A combination of the antibiotic compound and the miscible monomer is selected so that, preferably, a polymer of the polymerizable vinyl monomer, and the antibiotic compound are miscible at a polymerization temperature (heating temperature) to be described later.

The polymerizable vinyl monomer can contain a crosslinkable monomer as the miscible monomer.

The crosslinkable monomer is blended as necessary to adjust controlled release properties of the controlled release particles, and examples of the crosslinkable monomer include mono or polyethylene glycol di(meth)acrylate such as ethylene glycol di(meth)acrylate and diethylene glycol di(meth)acrylate; alkane diol di(meth)acrylate such as 1,3-propanediol di(meth)acrylate, 1,4-butanediol di(meth)acrylate, and 1,5-pentanediol di(meth)acrylate; alkane polyol poly(meth)acrylate such as trimethylolpropane tri(meth)acrylate and pentaerythritol tetra(meth)acrylate; allyl monomers such as allyl(meth)methacrylate, and triallyl(iso)cyanurate; and divinyl monomers such as divinylbenzene. Preferably, mono or polyethylene glycol di(meth)acrylate is used.

As the crosslinkable monomer, a monomer having a molecule structure that is similar to that of the miscible monomer excluding the crosslinkable monomer is selected to ensure miscibility of the antibiotic compound and the monomer mixture (polymerizable vinyl monomer) including the crosslinkable monomer; to be specific, when the miscible monomer excluding the crosslinkable monomer contains a (meth)acrylic acid ester monomer, preferably, mono or polyethylene glycol di(meth)acrylate is selected as the crosslinkable monomer.

The mixing ratio of the crosslinkable monomer relative to 100 parts by mass of the miscible monomer excluding the crosslinkable monomer is, for example, 1 to 100 parts by mass, preferably 10 to 80 parts by mass.

As the antibiotic compound and the polymerizable vinyl monomer, a combination of the following is selected: an antibiotic compound having a polar term $\delta_{p,compound}$ of, for example, 2 to 8[(J/cm$^3$)$^{1/2}$] and a hydrogen bonding term $\delta_{h,compound}$ of, for example, 5.5 to 9.5[(J/cm$^3$)$^{1/2}$] of the solubility parameter $\delta$ defined by Hansen and calculated by van Krevelen and Hoftyzer method; and a polymerizable vinyl monomer that produces a polymer having a polar term $\delta_{p,polymer}$ of, for example, 5 to 7[(J/cm$^3$)$^{1/2}$] and a hydrogen bonding term $\delta_{h,polymer}$ of 8 to 10[(J/cm$^3$)$^{1/2}$] of the solubility parameter $\delta$.

The indexes "compound" and "polymer" in each term $\delta$ ($\delta_p$ and $\delta_h$) represent the antibiotic compound and the polymer, respectively.

The polar term $\delta_p$ and the hydrogen bonding term $\delta_h$ of the solubility parameter $\delta$ defined by Hansen and calculated by van Krevelen and Hoftyzer method depend on the types and the number of the atomic group (including chemical bond or substituent), to be specific, represented by following formulas (1) and (2), respectively.

[Mathematical Formula 1]

$$\delta_p = \frac{\sqrt{\sum F_{pi}^2}}{V} \quad (1)$$

(where $F_p$ represents polar component of the molar attraction function, and V represents molar volume)

[Mathematical Formula 2]

$$\delta_h = \sqrt{\frac{\sum E_{hi}}{V}} \quad (2)$$

(where $E_h$ represents contribution of the hydrogen bonding forces to the cohesive energy, and V represents molar volume.)

Values of the above-described $F_p$, $E_h$, and V are described in "Properties of Polymers" (3rd Edition, Chapter 7, pp 189 to 225, written by van Krevelen, ELSEVIER, issued in 2003) by atomic group.

$F_p$ and $E_h$ of substituent —I, >Si<, =N— and ≡C— are not described in the above-described document, but calculated by professor Hideki Yamamoto of Kansai University by the following method.

First, an example of the calculation method for $F_p$ of substituent —I is given.

Ten compounds containing substituent —I described in "Hansen Solubility Parameters, A User's Handbook" (written by Charles Hansen, pp 347 to 483 (Appendix), CRC Press, issued in 2007) are randomly selected, and the left side of the above-described formula (1) is substituted by the value of compound $\delta_p$ described in the above-described document. Furthermore, the right side of the above-described formula (2) is substituted by values of V of all atomic groups of the ten compounds selected as described above, and $F_p$ of the atomic group excluding the substituent —I, while $F_p$ of the substituent —I in the right side is rendered unknown.

Then, the equation in which $\delta_p$ of the compound and V of all atomic groups are known, and $F_p$ of the atomic group excluding the substituent is known, and Fp of substituent —I is unknown is solved, and the average of the solution ($F_p$) of the ten compound as $F_p$ of substituent —I is calculated.

$F_p$ of the substituent >Si<, =N—, and ≡C— is also calculated in the above-described manner.

$E_h$ of the substituent —I, >Si<, =N—, and ≡C— can also be calculated in the above-described manner.

The above-described calculation process is recorded in a computer as a program, and optimized.

$F_p$ and $E_h$ of the substituent —I, >Si<, =N—, and ≡C— calculated as described above are noted below.

| | |
|---|---|
| —I | $F_p$: 0 (J$^{1/2}$ · cm$^{3/2}$ · mol$^{-1}$) |
| | $E_h$: 0 (J · mol$^{-1}$) |
| >Si< | $F_p$: 0 (J$^{1/2}$ · cm$^{3/2}$ · mol$^{-1}$) |
| | $E_h$: 0 (J · mol$^{-1}$) |
| =N— | $F_p$: 800 (J$^{1/2}$ · cm$^{3/2}$ · mol$^{-1}$) |
| | $E_h$: 3000 (J · mol$^{-1}$) |
| ≡C— | $F_p$: 0 (J$^{1/2}$ · cm$^{3/2}$ · mol$^{-1}$) |
| | $E_h$: 0 (J · mol$^{-1}$) |

Next, as an example of polymers, polymethyl methacrylate (PMMA), i.e., a polymer of methyl methacrylate, is given as an example, and a polar term $\delta_{p,PMMA}$ and a hydrogen bonding term $\delta_{h,PMMA}$ of the solubility parameter $\delta$ of polymethyl methacrylate is calculated.

1. Polar Term $\delta_p$ and Hydrogen Bonding Term $\delta_h$ of Homopolymer (1) Structural Formula of Polymethyl Methacrylate Polymethyl methacrylate is represented by formula (3) below.

[Chemical Formula 1]

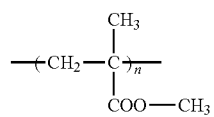

(3)

(where n represents degree of polymerization)

(2) Polar Term $\delta_{p,PMMMA}$ $F_p$ and V of atomic groups in the monomer unit (—CH$_2$—C(CH$_3$)COOCH$_3$—) of the above-described formula (3) are shown below.

| | |
|---|---|
| —CH$_3$ | $F_p$: 0 (J$^{1/2}$ · cm$^{3/2}$ · mol$^{-1}$) |
| | V: 33.5 (cm$^3$ · mol) |
| —CH$_2$— | $F_p$: 0 (J$^{1/2}$ · cm$^{3/2}$ · mol$^{-1}$) |
| | V: 16 (cm$^3$ · mol) |
| >C< | $F_p$: 0 (J$^{1/2}$ · cm$^{3/2}$ · mol$^{-1}$) |
| | V: −19.2 (cm$^3$ · mol) |
| —COO— | $F_p$: 490 (J$^{1/2}$ · cm$^{3/2}$ · mol$^{-1}$) |
| | V: 18 (cm$^3$ · mol) |

Therefore, polar term $\delta_{p,monomer\ unit}$ of the monomer unit is calculated, as shown in formula (4) below, to be 5.98 [(J/cm$^3$)$^{1/2}$].

[Mathematical Formula 3]

$$\delta_p = \frac{\sqrt{\sum F_{pi}^2}}{V}$$

$$= \frac{\sqrt{0^2 + 0^2 + 0^2 + 490^2}}{2 \times 33.5 + 16.1 + (-19.2) + 18}$$

$$= 5.98 \left[ (J/cm^3)^{1/2} \right] \quad (4)$$

Then, the polar term $\delta_{p, monomer\ unit}$ of the above-described monomer unit is rendered the polar term $\delta_{p,\ PMMA}$ of polymethyl methacrylate, having a repeating structure of the monomer unit.

(3) Hydrogen Bonding Term $\delta_{h,PMMA}$ $E_h$ of the atomic groups in the monomer unit (—CH$_2$—C(CH$_3$)COOCH$_3$—) of the above-described formula (3) is shown below.

| | |
|---|---|
| —CH$_3$ | $E_h$: 0 (J · mol$^{-1}$) |
| —CH$_2$— | $E_h$: 0 (J · mol$^{-1}$) |
| >C< | $E_h$: 0 (J · mol$^{-1}$) |
| —COO— | $E_h$: 7000 (J · mol$^{-1}$) |

Therefore, the hydrogen bonding term $\delta_{h,\ monomer\ unit}$ of the monomer unit is calculated, as shown in formula (5) below, to be $9.25[(J/cm^3)^{1/2}]$.

[Mathematical Formula 4]

$$\delta_h = \sqrt{\frac{\sum E_{hi}}{V}} \quad (5)$$

$$= \sqrt{\frac{0+0+0+7000}{2 \times 33.5 + 16.1 + (-19.2) + 18}}$$

$$= 9.25[(J/cm^3)^{1/2}]$$

Then, the above-described hydrogen bonding term $\delta_{h,polymer}$ of the monomer unit is rendered the hydrogen bonding term $\delta_{h,\ PMMA}$ of polymethyl methacrylate, having a repeating structure of the monomer unit.

2. Polar Term $\delta_p$ and Hydrogen Bonding Term $\delta_h$ of Copolymer

Next, polar term $\delta_p$ and hydrogen bonding term $\delta_h$ of a copolymer is calculated.

By multiplying the polar term $\delta_{p,\ monomer\ unit}$ of monomer units by the mass ratio of the monomer, and by adding these, the polar term $\delta_{p,\ copolymer}$ of the solubility parameter $\delta$ of the copolymer is calculated. Also, by multiplying the hydrogen bonding term $\delta_{h,\ monomer\ unit}$ of the monomer units by the mass ratio of the monomer, and adding these, the hydrogen bonding term $\delta_{h,\ copolymer}$ of the solubility parameter $\delta$ of the copolymer is calculated.

As an example of the copolymer, a polymethyl methacrylate-ethylene glycol dimethacrylate (PMMA-EGDMA), i.e., a copolymer of a monomer containing methyl methacrylate, and ethylene glycol dimethacrylate in a mass ratio of 70:30 (corresponds to the mass ratio of Examples 1 to 7 be described later), is used, and its polar term $\delta_{p,\ PMMA-EGDMA}$ and the hydrogen bonding twin $\delta_{h,\ PMMA-EGDMA}$ of the solubility parameter $\delta$ are calculated.

(1) Polar Term $\delta_{p,PMMA-EGDMA}$

The polar term $\delta_{p,\ MMA\ unit}$ of the monomer unit of methyl methacrylate is, as calculated above, $5.98[(J/cm^3)^{1/2}]$.

The polar term $\delta_p$, EDGMA of the monomer unit of ethylene glycol dimethacrylate is calculated in the same manner as above, and determined to be $5.37[(J/cm^3)^{1/2}]$.

The polar term $\delta_{p,\ PMMA-EGDMA}$ of the copolymer is calculated as shown in formula (6) below.

$$\delta_{p,PMMA-EGDMA} = (70/100)\delta_{p,MMA\ unit} + (30/100)\delta_{p,EGDMA\ unit} \quad (6)$$

-continued $$= (70/100) \times 5.98 + (30/100) \times 5.37$$

$$= 5.80[(J/cm^3)^{1/2}](70/100)$$

(2) Hydrogen Bonding Term $\delta_{h,PMMA-EGDMA}$

The hydrogen bonding term $\delta_{h,\ MMA\ unit}$ of the monomer unit of methyl methacrylate is $9.25[(J/cm^3)^{1/2}]$.

The hydrogen bonding term $\delta_{h,\ EGDMA}$ of the monomer unit of ethylene glycol dimethacrylate is $10.42[(J/cm^3)^{1/2}]$.

The hydrogen bonding term $\delta_{h,\ PMMA-EGDMA}$ of the copolymer is calculated as shown in formula (7) below.

$$\delta_{h,PMMA-EGDMA} = (70/100)\delta_{h,MMA\ unit} + (30/100)\delta_{h,EGDMA\ unit} \quad (7)$$

$$= (70/100) \times 9.25 + (30/100) \times 10.42$$

$$= 9.60[(J/cm^3)^{1/2}]$$

The polar term $\delta_{p,\ polymer}$ of the solubility parameter $\delta$ of the polymer is preferably 5 to $6.5[(J/cm^3)^{1/2}]$, and the hydrogen bonding term $\delta_{h,polymer}$ of the solubility parameter $\delta$ of the polymer is preferably 9 to $10[(J/cm^3)^{1/2}]$.

When the polar term $\delta_{p,polymer}$ and/or the hydrogen bonding term $\delta_{h,polymer}$ of the polymer are below the above-described range, the polymer becomes excessively hydrophobic, and sufficient miscibility with the antibiotic compound may not be obtained, and even if miscibility was obtained, the antibiotic compound leaks to the outside of the core during the suspension polymerization, making synthesis of controlled release particles in which the antibiotic compound is sufficiently encapsulated difficult.

On the other hand, when the polar term $\delta_{p,polymer}$ and/or the hydrogen bonding term $\delta_{h,polymer}$ of the polymer exceeds the above-described range, there may be a case where hydrophilicity of the polymer becomes excessively high and sufficient miscibility with the antibiotic compound cannot be obtained, and even if miscibility could be obtained, interfacial free energy with the aqueous phase in the suspension polymerization is lowered, and antibiotic compound leaks to the outside of the core during the suspension polymerization, making synthesis of the core in which the antibiotic compound is sufficiently encapsulated difficult.

3. Polar term $\delta_{p,compound}$ and Hydrogen Bonding Term $\delta_{h,compound}$ of Solubility $\delta$ of Antibiotic Compound The polar term $\delta_{p,compound}$ and the hydrogen bonding term $\delta_{h,compound}$ of the solubility $\delta$ of the antibiotic compound are also calculated in the same manner as that of the above-described monomer unit.

Table 1 shows the results of the calculated polar term $\delta_{p,compound}$ and hydrogen bonding term $\delta_{h,compound}$ of antibiotic compounds, i.e., IPBC, OIT, cyfluthrin, propiconazole, prochloraz, and flusilazole.

TABLE 1

| Antibiotic Compound | Polar Term $\delta p$, compound $[J/cm^3]^{1/2}$ | Hydrogen Bonding Term $\delta p$, compound $[J/cm^3]^{1/2}$ |
|---|---|---|
| IPBC | 3.23 | 7.83 |
| OIT | 5.47 | 5.87 |
| Cyfluthrin | 3.46 | 6.09 |
| Propiconazole | 6.55 | 9.44 |
| Prochloraz | 7.07 | 8.31 |
| Flusilazole | 5.95 | 6.85 |

The polar term $\delta_{p,compound}$ of solubility parameter $\delta$ of the antibiotic compound is preferably 3 to $7[(J/cm^3)^{1/2}]$ and the hydrogen bonding term $\delta_{h,compound}$ is preferably 5.8 to $9.5[(J/cm^3)^{1/2}]$.

When the polar term $\delta_{p,compound}$ and/or the hydrogen bonding term $\delta_{h,compound}$ of the antibiotic compound is below the above-described range, there may be a case where hydrophobicity of the antibiotic compound becomes excessively high and sufficient miscibility with the polymer cannot be obtained.

On the other hand, when the polar term $\delta_{p,compound}$ and/or the hydrogen bonding term $\delta_{h,compound}$ of the antibiotic compound exceed the above-described range, there may be a case where hydrophilicity of the antibiotic compound becomes excessively high and the antibiotic compound easily leaks to the outside of the core, making synthesis of the core in which the antibiotic compound is sufficiently encapsulated difficult.

4. Difference in Polar Term $\delta_p$ ($\Delta\delta_p$) and Difference in Hydrogen Bonding Term $\delta_h$ ($\Delta\delta_h$) of Solubility Parameter The value of $\Delta\delta_p(=\delta_{p,polymer}-\delta_{p,compound})$ deducting the polar term $\delta_{p,compound}$ of the antibiotic compound from the polar term $\delta_{p,polymer}$ of the solubility parameter $\delta$ of the polymer is, for example, $-2.5$ to $3.0[(J/cm^3)^{1/2}]$, preferably $-1.1$ to $2.7[(J/cm^3)^{1/2}]$.

The value of $\Delta\delta_h$ ($=\delta_{h,polymer}-\delta_{h,compound}$) deducting the hydrogen bonding term $\delta_{h,compound}$ of the antibiotic compound from the hydrogen bonding term $\delta_{h,polymer}$ of the polymer is, for example, $-1.1$ to $4.5[J/cm^3)^{1/2}]$, preferably 0 to $4.2[(J/cm^3)^{1/2}]$.

When $\Delta\delta_p$ and $\Delta\delta_h$ are within the above-described range, excellent miscibility of the antibiotic compound and the polymer can be ensured, ensuring excellent controlled release properties.

When the polar term $\delta_{p,compound}$ and the hydrogen bonding term $\delta_{h,compound}$ of the antibiotic compound are within the above-described range, and the polar term $\delta_{p,polymer}$ and the hydrogen bonding term $\delta_{h,polymer}$ of the polymer are within the above-described range, the antibiotic compound is defined as being miscible with the polymer without leaking from the core during suspension polymerization.

The ratio of the antibiotic compound relative to the polymerizable vinyl monomer is, on a mass basis (that is, parts by mass of the antibiotic compound/parts by mass of the polymerizable vinyl monomer), for example, 10/90 to 60/40 (that is, 0.11 to 1.5).

In particular, when the antibiotic compound is liquid at normal temperature (20 to 30° C., to be more specific, 25° C.), the mixing ratio of the antibiotic compound relative to the polymerizable vinyl monomer is, because the antibiotic compound works as a plasticizer for the polymer of the polymerizable vinyl monomer, on a mass basis, for example, 1/99 to 60/40 (that is, 0.01 to 1.5), preferably 5/95 to 50/50 (that is, 0.05 to 1.0).

When the antibiotic compound is solid at normal temperature, because the diffusing speed (controlled releasing speed) of the antibiotic compound becomes slower than the case where the antibiotic compound is liquid at normal temperature, the mixing ratio of the antibiotic compound relative to the polymerizable vinyl monomer is, on a mass basis, for example, 10/90 to 70/30 (that is, 0.11 to 2.33), preferably 10/90 to 60/40 (that is, 0.11 to 1.5).

The shell-forming component contains at least two components that are different from each other and that react by polycondensation or polyaddition, for example, a first shell-forming component and a second shell-forming component.

The first shell-forming component is substantially hydrophobic, and, to be specific, has a quite low water solubility at room temperature, to more be specific, for example, a solubility at room temperature of, on a mass basis, 1 part by mass/100 parts by mass of water (10000 ppm) or less, preferably 0.5 parts by mass/100 parts by mass of water (5000 ppm) or less, and more preferably 0.1 parts by mass/100 parts by mass of water (1000 ppm) or less.

The first shell-forming component is an oil-soluble compound that forms a shell by polymerizing (reacting) with the second shell-forming component, and examples thereof include polyisocyanate, polycarboxylic acid chloride, and polysulfonic acid chloride.

Examples of the polyisocyanate include aromatic polyisocyanate (aromatic diisocyanate) such as diphenylmethane diisocyanate, and toluenediisocyanate; aliphatic polyisocyanate (aliphatic diisocyanate) such as hexamethylene diisocyanate; alicyclic polyisocyanate (alicyclic diisocyanate) such as isophorone diisocyanate (IPDI), hydrogenated xylylenediisocyanate, and hydrogenated diphenylmethane diisocyanate; and aralkyl polyisocyanate (aralkyl diisocyanate) such as xylylenediisocyanate and tetramethylxylylenediisocyanate.

Examples also include multimers of the above-described polyisocyanates, to be specific, dimers, trimers (isocyanurate-group containing polyisocyanate, trimer modified substance), pentamers, and heptamers. Preferably, trimers, to be specific, a trimer of IPDI is used.

Furthermore, modified substance (excluding multimer) of the above-described polyisocyanate are also included, for example, polyol modified polyisocyanate.

Examples of the polycarboxylic acid chloride include sebacic acid dichloride, adipic acid dichloride, azelaic acid dichloride, terephthalic acid dichloride, and trimesic acid dichloride.

Examples of polysulfonic acid chloride include benzenesulfonyl dichloride.

The first shell-forming component may be used alone, or may be used in combination.

As the first shell-forming component, preferably, polyisocyanate, more preferably, a multimer of polyisocyanate is used.

The second shell-forming component is, before the interfacial polymerization, a water-soluble compound present in the aqueous phase. The second shell-forming component is an active hydrogen group-containing compound, and examples of such an active hydrogen group-containing compound include those compounds having an active hydrogen group such as a hydroxyl group and an amino group, to be specific, for example, polyamine, polyol, and water.

Examples of polyamines include diamines such as ethylene diamine, propylene diamine, hexamethylenediamine, diaminotoluene, phenylenediamine, and piperazine; triamines such as diethylene triamine; tetraamine such as triethylenetetramine; pentaamine such as tetraethylenepentamine; and hexamine such as pentaethylenehexamine. Preferably, triamine is used.

Examples of polyol include diols such as ethylene glycol, propanediol, 1,4-butanediol, 1,6-hexanediol, neopentyl glycol, diethylene glycol, triethylene glycol, dipropylene glycol, cyclohexanedimethanol, polyethylene glycol, and polypropylene glycol; triols such as glycerine, and trimethylolpropane; and tetraol such as pentaerythritol.

The second shell-forming component may be used alone, or may be used in combination.

Preferably, polyamine is used.

In the production method, in the first step, first, the first component is prepared as a hydrophobic solution.

The hydrophobic solution is prepared by blending the above-described antibiotic compound and the polymerizable vinyl monomer. To be specific, the hydrophobic solution is prepared by dissolving the antibiotic compound in the polymerizable vinyl monomer in the absence of the solvent.

With the hydrophobic solution, preferably, an initiator is blended.

Examples of the initiator include oil-soluble radical polymerization initiators, and examples of the radical polymerization initiator include organic peroxides such as dilauroyl peroxide (10 hours half-life temperature $T_{1/2}$: 61.6° C.), 1,1,3,3-tetramethylbutylperoxy-2-ethylhexanoate (10 hours half-life temperature $T_{1/2}$: 65.3° C.), t-hexylperoxy-2-ethylhexanoate (10 hours half-life temperature $T_{1/2}$: 69.9° C.), diisopropylperoxydicarbonate (10 hours half-life temperature $T_{1/2}$: 40.5° C.), and benzoylperoxyde (10 hours half-life temperature $T_{1/2}$: 73.6° C.); and azo compounds such as 2,2'-azobisisobutyronitrile (10 hours half-life temperature $T_{1/2}$: 60° C.), 2,2'-azobis(2,4-dimethylvaleronitrile)(10 hours half-life temperature $T_{1/2}$: 51° C.), and 2,2'-azobis(2-methylbutyronitrile)(10 hours half-life temperature $T_{1/2}$: 67° C.). Preferably, organic peroxide is used.

The 10 hours half-life temperature $T_{1/2}$ of the initiator is, for example, 40 to 90° C., preferably 50 to 80° C. The 10 hours half-life temperature $T_{1/2}$ of the initiator is determined from a graph obtained by plotting the time by which the concentration is reduced to half at arbitrary temperatures, and the temperature at which 10 hours value is rendered the 10 hours half-life temperature $T_{1/2}$.

The mixing ratio of the initiator relative to 100 parts by mass of the polymerizable vinyl monomer is, for example, 0.01 to 2 parts by mass, preferably 0.1 to 1 parts by mass.

The initiator is blended at the same time with the blending of the above-described antibiotic compound and the polymerizable vinyl monomer, or before or after the blending. Preferably, the initiator is dissolved, when the antibiotic compound is dissolved in the polymerizable vinyl monomer simultaneously.

The first shell-forming component can also be blended with the hydrophobic solution. That is, the hydrophobic solution can contain a portion of the second component (shell-forming component) (all or portion of the first shell-forming component) along with the first component.

The mixing ratio of the first shell-forming component to be blended with the hydrophobic solution relative to 100 parts by mass of the polymerizable vinyl monomer is, for example, 5 to 80 parts by mass, preferably 10 to 70 parts by mass, more preferably 20 to 60 parts by mass, particularly preferably 25 to 50 parts by mass.

In other words, the ratio of the first shell-forming component relative to the polymerizable vinyl monomer is, on a mass basis (that is, parts by mass of the first shell-forming component/parts by mass of the polymerizable vinyl monomer), for example, 0.05 to 0.8, preferably 0.1 to 0.7, more preferably 0.2 to 0.6, particularly preferably 0.25 to 0.5.

When the ratio is below the above-described range, the effects of suppressing the controlled release speed may become insufficient, and furthermore, the shell thickness becomes non-uniform, and may reduce re-dispersiveness (described later).

On the other hand, when the ratio exceeds the above-described range, the controlled release particles cannot release the antibiotic compound, and furthermore, the antibiotic compound content decreases excessively, and the controlled release particles may not be able to exhibit antibiotic properties.

Preparation of the hydrophobic solution may be performed, for example, at normal temperature, or as necessary, can be performed by heating to 30 to 100° C. Preferably, in view of suppressing thermal decomposition of the initiator, the hydrophobic solution is prepared at normal temperature without heating.

In the first step, next, the hydrophobic solution is suspended (aqueously dispersed) in water.

That is, the hydrophobic solution and water are blended, and the mixture is stirred homogeneously, thereby allowing the hydrophobic solution to be suspended. A suspension liquid of the hydrophobic solution is obtained in this manner.

Conditions for the suspension are not particularly limited. For example, the suspension may be performed at normal temperature, or can be performed by heating at 30 to 100° C. Preferably, in view of suppressing thermal decomposition of the initiator, and also suppressing the reaction, when the first shell-forming component to be blended in the hydrophobic solution reacts with water due to its reactivity, the suspension is performed without heating.

The mixing ratio of water relative to 100 parts by mass of the hydrophobic solution is, for example, 50 to 1500 parts by mass, preferably 100 to 1000 parts by mass, more preferably 120 to 500 parts by mass.

When the hydrophobic solution is suspended, for example, a dispersing agent is blended.

Examples of dispersing agents include water-soluble polymers such as polyvinyl alcohol (PVA, including partially saponified polyvinyl alcohol), polyvinyl pyrrolidone, gelatin, gum arabic, hydroxyethyl cellulose, hydroxypropyl cellulose, carboxymethyl cellulose, cationized starch, polyacrylic acid and its sodium salt, and styrene maleic acid copolymer and its sodium salt; and inorganic dispersing agents such as tribasic calcium phosphate, colloidal silica, montmorillonite, magnesium carbonate, aluminum hydroxide, and zinc white.

Of the dispersing agents, preferably, polyvinyl alcohol and tribasic calcium phosphate is used. When the tribasic calcium phosphate is used, and when the obtained controlled release particles are formulated into suspension formulation, re-dispersiveness of the suspension formulation is remarkably excellent, and when formulated into powder formulation (described later) or granular formulation (described later), re-dispersiveness of the powder formulation or granular formulation in water is excellent.

The mixing ratio of the dispersing agent relative to 100 parts by mass of the hydrophobic solution is, for example, 0.1 to 20 parts by mass, preferably 0.5 to 10 parts by mass.

When the hydrophobic solution is suspended, a surfactant can be used in combination along with the above-described dispersing agent.

The surfactant is blended to effectively prevent aggregation of the core in the suspension polymerization. Examples of the surfactant include anionic surfactants such as sodium dodecylbenzenesulfonate (DBN), sodium lauryl sulfate, sodium di-2-ethylhexyl sulfosuccinate, sodium dodecyl diphenyl ether disulphonate, sodium nonyl diphenyl ether sulfonate, sodium polyoxyethylene alkyl ether sulfonate, ammonium polyoxyethylene alkyl ether phosphate, and naphthalenesulfonic acid formaldehyde condensate sodium salt; and non-ionic surfactants such as polyoxyethylene lauryl ether, polyoxyethylenenonylphenylether, polyoxyethylene monostearate, polyoxyethylene sorbitan monooleate, and polyoxyethylene polyoxypropylene block copolymer. Preferably, anionic surfactants are used.

The mixing ratio of the surfactant relative to 100 parts by mass of the hydrophobic solution is, for example, 0.0001 to 1.0 parts by mass, preferably 0.001 to 0.1 parts by mass.

These dispersing agents and surfactants can be blended, for example, before or after the blending of the hydrophobic solution with water. Preferably, these dispersing agents and surfactants are blended in water before being blended with the hydrophobic solution. An aqueous solution or dispersion of the dispersing agent and the surfactant are prepared in this manner.

For the above-described suspension of the hydrophobic solution, for example, dispersers such as a homomixer, Disper, an ultrasonic homogenizer, a pressurized homogenizer, Milder, and a porous membrane injection disperser are used.

Preferably, Homo Mixer is used, and its number of revolution is, for example, 100 to 10000 rpm, preferably 1000 to 8000 rpm.

Then, by increasing the temperature of the suspension liquid to a predetermined temperature, suspension polymerization of the first component is performed.

In suspension polymerization, the polymerizable vinyl monomer is allowed to react (to be specific, vinyl polymerization) while stirring the suspension liquid so as to maintain the suspension state of the suspension liquid, thereby producing a polymer of the polymerizable vinyl monomer. Furthermore, because the ingredient, the polymerizable vinyl monomer, is in the hydrophobic phase (oil phase), it is called in situ polymerization.

To perform suspension polymerization, first, the temperature of the suspension liquid is increased so that the temperature of the suspension liquid is higher than the 10 hours half-life temperature $T_{1/2}$ of the initiator by, for example, 1 to 30° C., preferably 5 to 20° C.

To be specific, the increased temperature (that is, polymerization temperature) is, for example, 30 to 100° C., preferably 40 to 80° C., more preferably 50 to 70° C.

The polymerization temperature of the suspension polymerization is set, preferably, higher than the melting point of the above-described antibiotic compound.

In the suspension liquid whose temperature is increasing, the initiator undergoes thermal decomposition at a certain temperature, causing suspension polymerization to start.

The temperature (starting temperature) $T_i$ at which the suspension polymerization starts is, for example, expressed as formula (1) below in relation to the above-described 10 hours half-life temperature $T_{1/2}$ of the initiator.

$$T_{1/2}-10 \leq T_i \leq T_{1/2}+10 \quad (1)$$

(where $T_i$ represents the starting temperature of the suspension polymerization, and $T_{1/2}$ represents the 10 hours half-life temperature of the initiator.)

The pressure at the time of suspension polymerization is not particularly limited, and suspension polymerization is carried out at normal pressure. Or, the suspension polymerization is carried out at high pressure. Preferably, the suspension polymerization is carried out at normal pressure.

The suspension polymerization is carried out, for example, under an atmosphere of inert gas such as nitrogen.

The polymerization time of the suspension polymerization is, for example, 1 hour or more, preferably, 3 hours or more, more preferably 4 hours or more, and usually 10 hours or less. The polymerization time of the suspension polymerization is, for example, below 3 hours, or can be set to 2 hours or less.

When the polymerization time of the suspension polymerization is below the above-described lower limit, the polymerization time becomes excessively short, and therefore the remaining polymerizable vinyl monomer and the first shell-forming component are present at the core surface and also slightly inside thereof to be miscible with each other, and the following interfacial polymerization progresses along with polymerization of the remaining polymerizable vinyl monomer.

The above-described suspension polymerization forms a core containing the antibiotic compound and a polymer of the polymerizable vinyl monomer.

During the suspension polymerization, the polymer of the polymerizable vinyl monomer is, for example, being miscible with the antibiotic compound. That is, the polymer is dissolved in the antibiotic compound to form an antibiotic compound solution of the polymer, and the antibiotic compound solution is suspended in an aqueous phase.

Regarding the polymerizable vinyl monomer, for example, as described above, for example, a combination of the polymer of the polymerizable vinyl monomer and the antibiotic compound are selected so that they are miscible with each other at the above-described polymerization temperature during the suspension polymerization, and therefore during the suspension polymerization, phase separation does not easily occur, and the reaction progresses under a state where the polymer (polymer during reaction) is dissolved in the antibiotic compound, or the polymer (polymer during reaction) is swelled in relation to the antibiotic compound, thus allowing production of a core in which a homogenous phase is formed.

Thereafter, the second component is subjected to interfacial polymerization, thereby carrying out the second step.

That is, when the hydrophobic solution contains the first shell-forming component in advance, the first shell-forming component in the core is allowed to react with the second shell-forming component. Furthermore, the interfacial polymerization in the second step is started when the first polymerizable vinyl monomer is reduced along with the progress of the suspension polymerization of the first step.

To be specific, by adding the second shell-forming component to the suspension liquid in which suspension polymerization progresses, interfacial polymerization is allowed to start. In this manner, the interfacial polymerization of the second component starts after the start of the suspension polymerization of the first step.

The mixing ratio of the second shell-forming component is set so that the equivalence ratio of the isocyanate group (isocyanate group/amino group) of the first shell-forming component relative to the amino group (primary amino group and secondary amino group) of the second shell-forming component is, for example, 0.4 to 1.2, preferably 0.6 to 1.0, more preferably 0.7 to 0.9.

The second shell-forming component is, preferably, diluted with water to prepare an aqueous solution of the second shell-forming component, and the aqueous solution of the second shell-forming component is added to the suspension liquid in which suspension polymerization is in progress.

Alternatively, an emulsified liquid of the first shell-forming component is prepared, and the prepared emulsified liquid and the second shell-forming component (aqueous solution of the second shell-forming component) can be blended with the suspension liquid to allow them to react. In this case, the emulsified liquid of the first shell-forming component is added to the suspension liquid, and by adding the second shell-forming component after the first shell-forming component is attached or absorbed on the surface of the polymer (core), interfacial polymerization is caused at the surface of the polymer (core).

To the aqueous solution of the second shell-forming component, a silane coupling agent can also be blended.

Examples of the silane coupling agent include an alkoxysilyl compound having at least a primary amino group, for example, an alkoxysilyl group-containing monoamine such as γ-aminopropyltriethoxysilane (3-aminopropyltriethoxysilane), and N-phenyl-γ-aminopropyltrimethoxysilane.

The mixing ratio of the silane coupling agent is, for example, when polyisocyanate is used as the first shell-forming component, and polyamine is used as the second shell-forming component, without changing the equivalence ratio of the isocyanate group relative to the amino group as described above, the ratio by which a portion of the second shell-forming component is replaced with the silane coupling agent.

The mixing ratio of the silane coupling agent relative to 100 parts by mass of the second shell-forming component is, for example, 0.5 to 20 parts by mass, preferably 2 to 10 parts by mass.

In the interfacial polymerization, the first shell-forming component present in the core (polymer) is allowed to react with the second shell-forming component in the aqueous phase at the surface of the polymer particles.

The interfacial polymerization can be performed, for example, at the same temperature with the polymerization temperature of the first step (suspension polymerization), or, can be performed at a temperature higher than the polymerization temperature of the first step (suspension polymerization). Such a temperature is, relative to the polymerization temperature of the first step, for example, a temperature higher by 1 to 20° C., preferably a temperature higher by 2 to 15° C., more preferably, a temperature higher by 5 to 10° C.

The polymerization time of the interfacial polymerization is, for example, 0.1 to 8 hours, preferably 0.5 to 6 hours, more preferably 1 to 4 hours.

When the polymerization time of the interfacial polymerization is within the above-described range, interfacial polymerization can be completed thoroughly.

Completion of the interfacial polymerization is confirmed, when the first shell-forming component is polyisocyanate, by disappearance of absorption in infrared absorption spectrum of the isocyanate group derived from polyisocyanate.

Completion of the interfacial polymerization can also be confirmed, when the second shell-forming component is polyamine, by a decrease of pH of the suspension liquid to a value near that before the addition of polyamine.

By subjecting the second component to interfacial polymerization to perform the second step, a shell covering the core can be formed.

The polymerizable vinyl monomer remaining at the time of start of the interfacial polymerization is present so as to be miscible with the first shell-forming component, and the interfacial polymerization of the second step progresses along with polymerization of the remaining polymerizable vinyl monomer.

Figure 5:
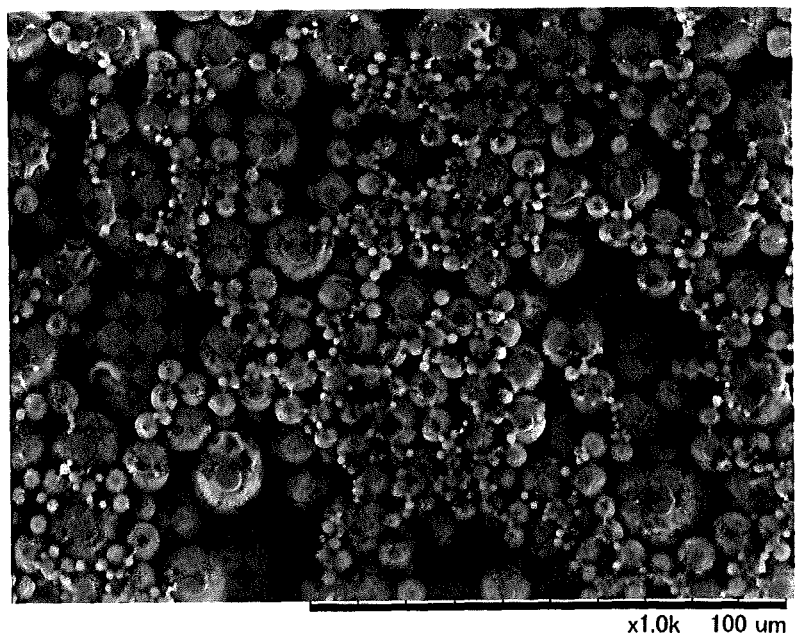
FIG. 5 shows an image-processed SEM photograph of controlled release particles of Example 5.

Thus, when the polymerization time of the suspension polymerization is short (to be specific, below 3 hours, or even within 2 hours), a comparatively large amount of the polymerizable vinyl monomer remains. Therefore, the first shell-forming component is in a solution state, and phase separation from the core containing the polymer formed from suspension polymerization occurs: as shown in the TEM photograph of FIG. 14, the shell (3) has a smooth surface along with the periphery of the core (2). Therefore, as shown in the SEM photograph of FIG. 5, the controlled release particles are formed into a generally spherical shape.

On the other hand, when the polymerization time of the suspension polymerization is long (to be specific, 3 hours or more, even 4 hours or more), a comparatively small amount of the polymerizable vinyl monomer remains, or substantially does not remain (substantially all undergone suspension polymerization), and therefore the first shell-forming component is in a state of a high viscosity solution, or a solid phase state, and phase separation from the core containing the polymer formed from suspension polymerization occurs. Therefore, as shown in FIG. 12 and FIG. 13, at the surface of the core (2), the first shell-forming component is partially present, and phase separation occurs to cause uneven distribution at the surface of the core (2). As a result, the shell (3) formed by interfacial polymerization is formed to have a non-uniform thickness along with the periphery of the core (2).

Figure 1:
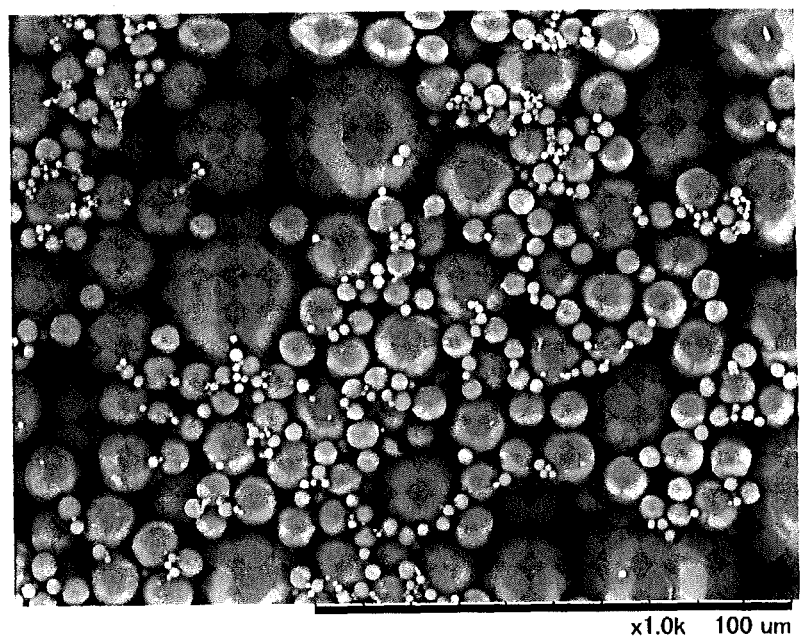
FIG. 1 shows an image-processed SEM photograph of controlled release particles of Example 1.
Figure 2:
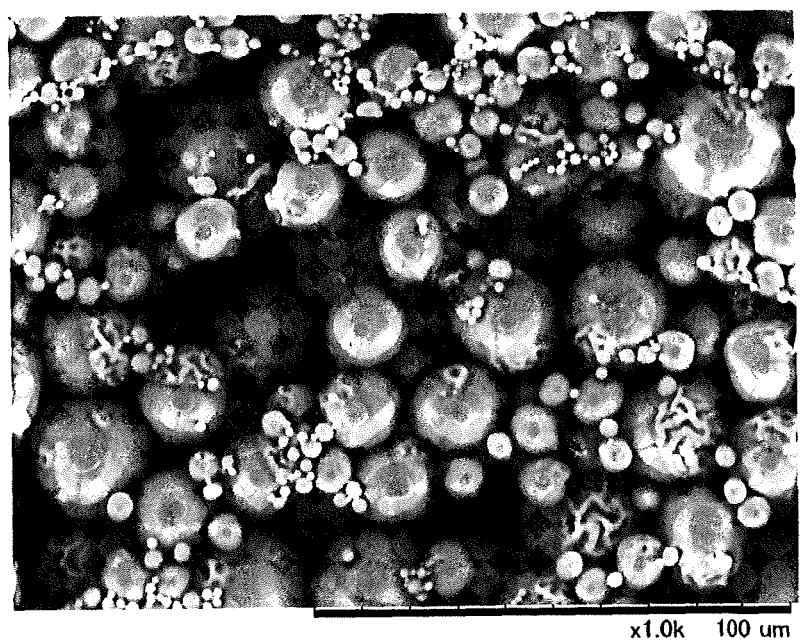
FIG. 2 shows an image-processed SEM photograph of controlled release particles of Example 2.
Figure 3:
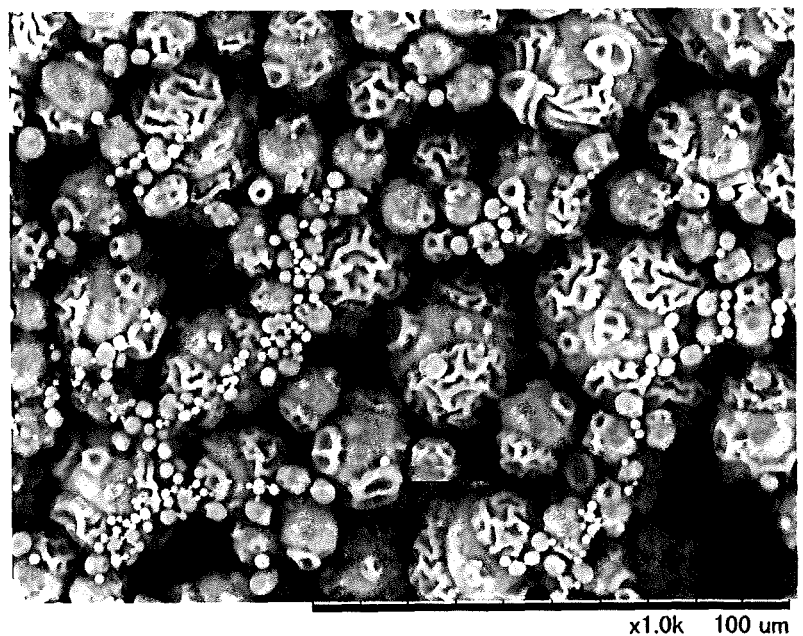
FIG. 3 shows an image-processed SEM photograph of controlled release particles of Example 3.
Figure 4:
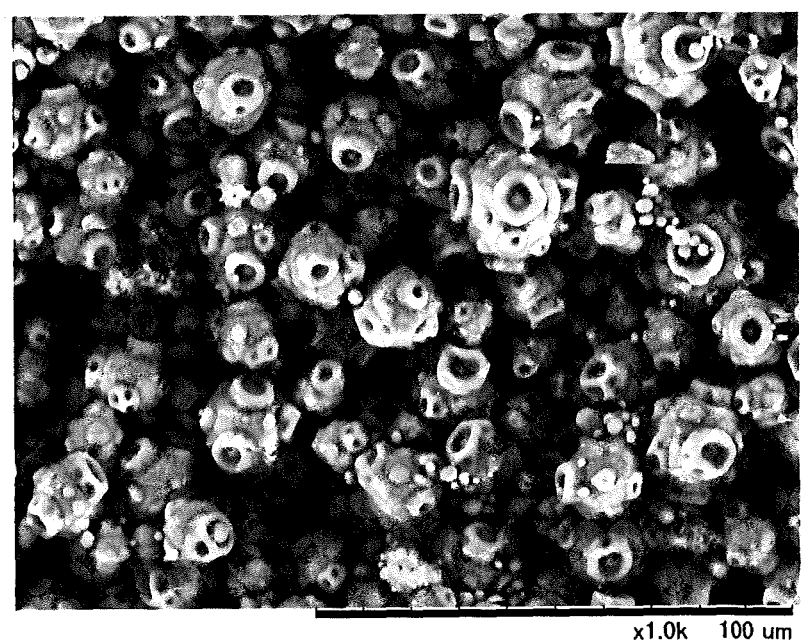
FIG. 4 shows an image-processed SEM photograph of controlled release particles of Example 4.

In such a case, as shown in the TEM photographs of FIG. 12 and FIG. 13, and the SEM photographs of FIG. 3 and FIG. 4, the shell (2) is formed with a projected portion (4) that projects outwardly. The projected portion (4) is formed in a plural number along with the circumferential direction of the shell (2) in spaced-apart relation.

Thus, when the controlled release particles (1) are formulated into suspension formulation, re-dispersiveness of the suspension formulation is improved, and occurrence of caking can be prevented.

Thereafter, the suspension liquid after the reaction is cooled, for example, by allowing the suspension liquid after reaction to stand to cool, or by water.

The cooling temperature is, for example, room temperature (20 to 30° C., to be more specific, 25° C.).

After the cooling, the antibiotic compound is, when the antibiotic compound is liquid at room temperature, being miscible with the polymer in the core.

Or, after the cooling, when the antibiotic compound is solid at room temperature, in the polymer of the core, the miscible state is frozen, thereby keeping a homogenous state.

On the other hand, the antibiotic compound is, preferably, not being miscible with the shell.

In this manner, a suspension liquid including the controlled release particles containing the core and the shell can be obtained.

The particle size of the controlled release particles is not particularly limited, and the average particle size (median size) is, for example, 1 μm to 1 mm, preferably 2 μm to 100 μm.

In this manner, a suspension liquid in which the controlled release particles are suspended is produced, the controlled release particles including a core containing the polymer of the polymerizable vinyl monomer and the antibiotic compound, and a shell covering the core.

Then, to the suspension liquid containing the controlled release particles, as necessary, known additives such as a thickening agent, an antifreezing agent, an antiseptic, a microbial growth inhibitor, and a specific gravity adjuster are blended appropriately.

The thus obtained controlled release particles may be used as is (suspension liquid), that is, may be used as suspension formulation, or for example, may be formulated into a known form such as powder formulation or granular formulation, after solid-liquid separation by filtration and/or centrifugal separation, etc. and used. As necessary, the controlled release particles can be washed with water and/or acid. Furthermore, the suspension liquid can be dried by spraying or by air as is, to be formulated into forms such as powder formulation or granular formulation.

The suspension formulation has a solid content concentration (controlled release particles concentration) of, for example, 1 to 50 mass %, preferably 5 to 40 mass %.

The suspension formulation has an antibiotic compound concentration of, for example, 0.5 to 40 mass %, preferably 1 to 25 mass %.

Meanwhile, powder formulation is excellent in flowability particularly when tribasic calcium phosphate is used as the dispersing agent. By dispersing or suspending the powder formulation in water again, water dispersion formulation or suspension formulation can be prepared again. Thus, the powder formulation is excellent in re-dispersibility in water or forming re-suspension.

Thus, by preparing the controlled release particles as powder formulation at the time of transportation, and preparing (re-formulation, reproduction) the powder formulation again as water dispersion or suspension, the transportation costs can be reduced, and furthermore, its application can be expanded.

In the above-described production method, the interfacial polymerization of the second step is started after the start of the suspension polymerization of the first step, and therefore the shell reliably covers the core containing the antibiotic compound and the polymer.

Thus, controlled release particles of the present invention having excellent controlled release properties, and capable of exhibiting excellent lasting effects can be obtained by suppressing the releasing speed of the antibiotic compound. By controlled release properties, what is meant is that the encapsulated compound can be released gradually.

When the aqueous solution of the second shell-forming component contains a silane coupling agent (alkoxysilyl compound having a primary amino group), a silanol group derived from the silane coupling agent is present in the shell, and the silanol group is capable of reacting with inorganic substance (to be specific, metal, metal oxide, etc.) or organic substance (to be specific, cellulose forming paper or lumber, etc.). Thus, when the controlled release particles are added (blended) to, for example, paint, sealant, or adhesive and used, the controlled release particles are capable of chemically bonding with the above-described base material composed of the above-described inorganic substance or organic substance, and antibiotic properties can be kept for a long period of time.

In the above-described embodiment, in the second step, the interfacial polymerization is started after the start of the suspension polymerization of the first step. However, the start of the interfacial polymerization is not limited to the above-described timing, and for example, the interfacial polymerization of the second step can also be started simultaneously with the start of the suspension polymerization of the first step.

That is, in the above-described embodiment, while the temperature of the suspension liquid is increased in the first step, when the temperature of the suspension liquid reached suspension polymerization start temperature $T_i$, the second shell-forming component (to be specific, aqueous solution of the second shell-forming component) is added to the suspension liquid.

By conducting the interfacial polymerization simultaneously with the suspension polymerization, when the polymerization speed of the suspension polymerization is faster than that of the interfacial polymerization, first, the core can be formed by suspension polymerization, while reliably forming the shell at the surface thereof.

On the other hand, in the case where the interfacial polymerization in the second step is started after the start of the suspension polymerization of the first step, and if the suspension polymerization is substantially completed before the start of the interfacial polymerization, stain on the core (pink stain, etc.) due to the active hydrogen group (to be specific, amino group) of the second shell-forming component (to be specific, polyamine, etc.) can be effectively prevented.

The controlled release speed of, the controlled release particles of the present invention is, as illustrated in Examples below, controlled by the ratio of the remaining polymerizable vinyl monomer (that is, ratio of the remaining polymerizable vinyl monomer relative to the charged polymerizable vinyl monomer. Hereinafter may be referred to as remaining monomer rate.) at the start of the interfacial polymerization of the second step.

That is, when the remaining monomer rate is 100%, that is, when the interfacial polymerization is conducted (started) at the same time with the suspension polymerization, the controlled release speed of the controlled release particles is the fastest. When the remaining monomer rate is substantially 0%, that is, when the interfacial polymerization is conducted (started) after the completion (finalization) of the suspension polymerization, the controlled release speed of the controlled release particles is the slowest. That is, as the remaining monomer rate at the start of the interfacial polymerization approaches 0% from 100%, the controlled release speed of the obtained controlled release particles slows accordingly.

Furthermore, depending on the application of the controlled release particles, in the case where the conditions are such that the controlled release speed easily gets faster, for example, when the controlled release particles are present in the presence of a solvent, or when the controlled release particles are used at high temperature, the core-shell structured controlled release particles of the present invention including a core containing an antibiotic compound and a shell that covers the core are suitably used.

Furthermore, when the remaining monomer rate is substantially 0%, as shown in the TEM photograph of FIG. 12 and FIG. 13, and the SEM photographs of FIG. 3 and FIG. 4, projected portions (4) are reliably formed, and therefore when the controlled release particles are formulated into suspension formulation, re-dispersiveness of the suspension formulation is also excellent.

EXAMPLES

Details of the abbreviations used in Examples and Comparative Examples are shown below.

IPBC: trade name "Fungitrol 400", 3-iodo-2-propynylbutylcarbamate, molecular weight 281, melting point: 60° C., water solubility: 150 ppm, polar term $\delta_{p,compound}$ of solubility parameter $\delta$: 3.23$[(J/cm^3)^{1/2}]$, hydrogen bonding term $\delta_{h,compound}$ of solubility parameter $\delta$: 7.83$[(J/cm^3)^{1/2}]$, manufactured by International Specialty Products Inc.

OIT: trade name "KATHON 893T" ("KATHON" is registered trademark), 2-n-octyl-4-isothiazoline-3-one, molecular weight 213, melting point: below 20° C., water solubility: 300 ppm, polar term $\delta_{p,compound}$ of solubility parameter $\delta$: 5.47$[(J/cm^3)\delta^{1/2}]$, hydrogen bonding term $\delta_{h,compound}$ of solubility parameter $\delta$: 5.87$[(J/cm^3)^{1/2}]$, manufactured by Rohm and Haas Company.

Propiconazole: 1-[2-(2,4-dichlorophenyl)-4-n-propyl-1,3-dioxolane-2-ylmethyl]-1H-1,2,4-triazole, molecular weight 342, melting point: below 20° C., water solubility: 110ppm, polar term $\delta_{p,compound}$ of solubility parameter $\delta$: 6.55 $[(J/cm^3)^{1/2}]$, hydrogen bonding term $\delta_{h,compound}$ of solubility parameter $\delta$: 9.44$[(J/cm^3)^{1/2}]$, manufactured by HAKKO TSUSHO CO.,LTD.

Flusilazole: bis(4-fluorophenyl)methyl (1H-1,2,4-triazole-1-ylmethylsliane), molecular weight 315, melting point: 54° C., water solubility: 45 ppm, polar term $\delta_{p,compound}$ of solubility parameter $\delta$: 5.95$[(J/cm^3)^{1/2}]$, hydrogen bonding term $\delta_{h,compound}$ of solubility parameter δ: 6.85[(J/cm³)$^{1/2}$], manufactured by ARBROWN CO., LTD.

Prochloraz: N-propyl-N-[2-(2,4,6-trichloro-phenoxy) ethyl] imidazole-1-carboxamide, molecular weight 375, melting point 45 to 52° C., water solubility: 55 ppm, polar term $\delta_{p,compound}$ of solubility parameter δ: 7.07[(J/cm³)$^{1/2}$], hydrogen bonding term $\delta_{hd\ h,compound}$ of solubility parameter δ: 8.31[(J/cm³)$^{1/2}$], manufactured by Maruzen Chemicals Co., Ltd, Cyfluthrin: trade name "Preventol HS 12" ("Preventol" is registered trademark), (RS)-α-cyano-4-fluoro-3-phenoxybenzyl-(1RS,3RS)-(1RS,3RS)-3-(2,2-dichlorovinyl)-2,2-dimethylcyclopropane carboxylate, molecular weight 434, water solubility: 1 to 2 ppb, mixture of isomer I (melting point 57° C.), isomer II (melting point 74° C.), isomer III (melting point 66° C.), and isomer IV (melting point 102° C.), polar term $\delta_{p,compound}$ of solubility parameter δ: 3.46[(J/cm³)$^{1/2}$], hydrogen bonding term $\delta_{h,compound}$ of solubility parameter δ: 6.09[(J/cm³)$^{1/2}$], manufactured by LANXESS.

Methyl methacrylate: trade name "ACRYESTER M" ("ACRYESTER" is registered trademark), water solubility: 1.6 mass%, polar term $\delta_{p,monomer\ unit}$ of solubility parameter δ as monomer unit: 6.69[(J/cm³)$^{1/2}$], hydrogen bonding term $\delta_{h,monomer\ unit}$ of solubility parameter δ as monomer unit: 9.78[(J/cm³)$^{1/2}$], manufactured by Mitsubishi Rayon Co., Ltd.

Methacrylic acid: water solubility: 8.9 mass%, polar term $\delta_{p\ unit}$ of solubility parameter δ as monomer unit: 7.13 [(J/cm³)$^{1/2}$], hydrogen bonding term $\delta_{h,monomer\ unit}$ of solubility parameter δ as monomer unit: 13.03[(J/cm³)$^{1/2}$], manufactured by Mitsubishi Rayon Co., Ltd.

Ethylene glycol dimethacrylate: trade name "Light Ester EG", water solubility: 5.37ppm, polar term $\delta_{p,monomer\ unit}$ of solubility parameter δ as monomer unit: 5.37[(J/cm³)$^{1/2}$], hydrogen bonding term $\delta_{h,monomer\ unit}$ of solubility parameter δ as monomer unit: 10.42[(J/cm³)$^{1/2}$], manufactured by Kyoeisha Chemical Co., Ltd.

T-1890: trade name "VESTANAT T 1890/100" ("VESTANAT" is registered trademark), trimer of isophorone diisocyanate (IPDI), first shell-forming component, melting point 110 to 120° C., water solubility: 20ppm, manufactured by Evonik Industries AG.

Dilauroyl peroxide: trade name "PEROYL® L"("PEROYL" is registered trademark), 10hours half-life temperature $T_{1/2}$: 61.6° C., manufactured by NOF CORPORATION Dibutyltin dilaurate: chemical reagent, polyaddition catalyst, manufactured by Wako Pure Chemical Industries, Ltd.

PVA-217: trade name "Kuraray Poval 217", partially saponified polyvinyl alcohol, manufactured by Kuraray Co., Ltd.

TCP-10U: trade name, a suspension liquid of 10% tribasic calcium phosphate (3[Ca$_3$(PO$_4$)$_2$].Ca(OH)$_2$) in water, manufactured by Matsuo Yakuhin Sangyo K. K.

DBN: trade name "NEOPELEX No.6 powder" ("NEOPELEX" is registered trademark), sodium dodecylbenzene sulphonate, manufactured by Kao Corporation.

Pelex SS-L: trade name ("Pelex" is registered trademark), sodium dodecyl diphenyl ether disulphonate, manufactured by Kao Corporation.

Diethylene triamine: Wako 1st grade, second shell-forming component, manufactured by Wako Pure Chemical Industries, Ltd.

Example 1

(Formulation of Suspension Formulation Including IPBC-containing Controlled Release Particles)
(Interfacial polymerization is started after the start of suspension polymerization)

A 200 mL beaker (1) was charged with 40 g of IPBC, 35 g of methyl methacrylate, 15 g of ethylene glycol dimethacrylate, 10 g of T-1890, and 300 mg of dilauroyl peroxide, and then the mixture was stirred at room temperature, thereby preparing a homogeneous hydrophobic solution.

Separately, a 500 mL beaker (2) was charged with 233 g of ion-exchange water, 40 g of a solution of 10 mass % PVA-217 in water, and 200 mg of a solution of 5 mass % DBN in water, and then the mixture was stirred at room temperature, thereby producing a homogeneous aqueous solution.

Then, the hydrophobic solution was added to the 500 mL beaker (2), and the mixture was stirred with T.K. Homo Mixer MARK Model 2.5 (manufactured by PRIMIX Corporation) at a number of revolution of 3000 rpm for 10 min, thereby suspending the hydrophobic solution, and preparing a suspension liquid.

Thereafter, the suspension liquid was transferred to a 500 mL, 4-neck flask equipped with a stirrer, a reflux condenser, a thermometer, and a nitrogen inlet tube, and subjected to suspension polymerization for three hours under nitrogen gas current, while stirring and increasing the temperature to 70° C.

Thereafter, interfacial polymerization was conducted. To be specific, an aqueous solution of diethylene triamine in which 1.2 g of diethylene triamine was diluted in 25 g of ion-exchange water was added to the above-described suspension liquid, and the temperature of the suspension liquid was increased to 75° C., and then kept at 75° C.

After elapse of 4 hours from the start of interfacial polymerization, the suspension liquid after the reaction was cooled to 30° C. or less.

A suspension liquid (suspension formulation) of controlled release particles including a core containing IPBC and a shell covering the core was obtained in this manner.

Example 2

(Formulation of Suspension Formulation Including IPBC-Containing Controlled Release Particles)
(Interfacial Polymerization is Started after the Start of Suspension Polymerization)

A suspension liquid (suspension formulation) of controlled release particles including a core containing IPBC and a shell covering the core was obtained by sequentially conducting suspension polymerization and interfacial polymerization in the same manner as in Example 1, except that the amounts of methyl methacrylate, ethylene glycol dimethacrylate, and T-1890 charged in the hydrophobic solution were changed to 31.5 g, 13.5 g, and 15 g, respectively, and the amount of diethylene triamine in the aqueous solution of diethylene triamine added at the start of the interfacial polymerization was changed to 1.8 g.

Example 3

(Formulation of Suspension Formulation Including IPBC-Containing Controlled Release Particles)
(Interfacial Polymerization is Started after the Start of Suspension Polymerization)

A suspension liquid (suspension formulation) of controlled release particles including a core containing IPBC and a shell covering the core was obtained by sequentially conducting suspension polymerization and interfacial polymerization in the same manner as in Example 1, except that the amounts of methyl methacrylate, ethylene glycol dimethacrylate, and T-1890 charged in the hydrophobic solution were changed to 28 g, 12 g, and 20 g, respectively, and the amount of diethylene triamine in the aqueous solution of diethylene triamine added at start of the interfacial polymerization was changed to 2.4 g.

Example 4

(Formulation of Suspension Formulation Including IPBC-containing Controlled Release Particles)
(Interfacial Polymerization is Started after the Start of Suspension Polymerization)

A suspension liquid (suspension formulation) of controlled release particles including a core containing IPBC and a shell covering the core was obtained by sequentially conducting suspension polymerization and interfacial polymerization in the same manner as in Example 1, except that the amounts of IPBC, methyl methacrylate, ethylene glycol dimethacrylate, and T-1890 charged in the hydrophobic solution were changed to 45 g, 28 g, 12 g, and 15 g, respectively, and the amount of the ion-exchange water in the aqueous solution was changed to 133 g, and furthermore, the number of revolution at the time of suspension of the hydrophobic solution with T.K.Homo Mixer MARK Model 2.5 (manufactured by PRIMIX Corporation) was changed to 4000 rpm, and furthermore, the amount of diethylene triamine in the aqueous solution of diethylene triamine added at the start of interfacial polymerization was changed to 1.8 g.

Example 5

(Formulation of Suspension Formulation Including IPBC-Containing Controlled Release Particles)
(Interfacial Polymerization is Started after the Start of Suspension Polymerization)

A suspension liquid (suspension formulation) of controlled release particles including a core containing IPBC and a shell covering the core was obtained by sequentially conducting suspension polymerization and interfacial polymerization in the same manner as in Example 2, except that the polymerization time of the suspension polymerization was changed from 3 hours to 2 hours.

Example 6

(Formulation of Suspension Formulation Including IPBC-Containing Controlled Release Particles)
(Suspension Polymerization and Interfacial Polymerization were Simultaneously Started)

A suspension liquid (suspension formulation) of controlled release particles containing IPBC was produced in the same manner as in Example 2, except that the suspension polymerization and the interfacial polymerization were simultaneously started, and their polymerization time was set to 7 hours.

To be specific, the interfacial polymerization and the suspension polymerization were simultaneously started by increasing the temperature of the suspension liquid to 70° C. and adding the aqueous solution of diethylene triamine.

Thereafter, temperature of the suspension liquid was kept at 75° C.

After elapse of 7 hours from the start of the suspension polymerization and the interfacial polymerization, the suspension liquid after the reaction was cooled to 30° C. or less.

The suspension liquid (suspension formulation) of controlled release particles including a core containing IPBC, and a shell covering the core was obtained in this manner.

The obtained suspension liquid was stained with pink color.

Example 7

(Formulation of Suspension Formulation Including IPBC-Containing Controlled Release Particles)
(Interfacial Polymerization is Started after the Start of Suspension Polymerization)

A suspension liquid (suspension formulation) of controlled release particles including a core containing IPBC and a shell covering the core was obtained by sequentially conducting suspension polymerization and interfacial polymerization in the same manner as in Example 2, except that 40 g of TCP-10U and 200 mg of an aqueous solution of 5% Pelex SS-L were charged instead of 40 g of a solution of 10 mass % PVA-217 in water, and 200 mg of a solution of 5 mass % DBN in water in the aqueous solution.

Example 8

(Formulation of Suspension Formulation Including OIT-Containing Controlled Release Particles)
(Interfacial Polymerization is Started after the Start of Suspension Polymerization)

A 200 mL beaker (1) was charged with 40 g of OIT, 27 g of methyl methacrylate, 4.5 g of methacrylic acid, 13.5 g of ethylene glycol dimethacrylate, 15 g of T-1890, and 300 mg of dilauroyl peroxide, and then the mixture was stirred at room temperature, thereby preparing a homogeneous hydrophobic solution.

Separately, a 500 mL beaker (2) was charged with 230 g of ion-exchange water, 40 g of TCP-10U, and 200 mg of an aqueous solution of 5 mass % Pelex SS-L, and the mixture was stirred at room temperature, thereby producing a homogenous suspension liquid.

Then, the hydrophobic solution was added to the 500 mL beaker (2), and the mixture was stirred with T.K.Homo Mixer MARK Model 2.5 (manufactured by PRIMIX Corporation) at a number of revolution of 3000 rpm for 10 min, thereby suspending the hydrophobic solution, and preparing the suspension liquid.

Thereafter, the suspension liquid was transferred to a 500 mL, 4-neck flask equipped with a stirrer, a reflux condenser, a thermometer, and a nitrogen inlet tube, and subjected to suspension polymerization for three hours under nitrogen gas current, while stirring and increasing the temperature to 70° C. Thereafter, interfacial polymerization was conducted.

To be specific, an aqueous solution of diethylene triamine in which 1.8 g of diethylene triamine was diluted in 25 g of ion-exchange water was added to the suspension liquid, and the temperature of the suspension liquid was increased to 75° C., and then kept at 75° C.

After elapse of 4 hours from the start of interfacial polymerization, the suspension liquid after the reaction was cooled to 30° C. or less.

The suspension liquid (suspension formulation) of controlled release particles including a core containing OIT, and a shell covering the core was obtained in this manner.

Example 9

(Formulation of Suspension Formulation Including IPBC-Containing Controlled Release Particles)
(Interfacial Polymerization is Started after the Start of Suspension Polymerization)

A 200 mL beaker (1) was charged with 25 g of IPBC, 50 g of methyl methacrylate, 10 g of ethylene glycol dimethacrylate, 15 g of T-1890, and 300 mg of dilauroyl peroxide, and then the mixture was stirred at room temperature, thereby preparing a homogeneous hydrophobic solution.

Separately, a 500 mL beaker (2) was charged with 82.7 g of ion-exchange water, 40 g of TCP-10U, and 200 mg of an aqueous solution of 5 mass % of Pelex SSL, and the mixture was stirred at room temperature, thereby producing a homogenous suspension liquid.

Then, the hydrophobic solution was added to the 500 mL beaker (2), and the mixture was stirred with T.K. Homo Mixer MARK Model 2.5 (manufactured by PRIMIX Corporation) at a number of revolution of 4000 rpm for 10 min, thereby suspending the hydrophobic solution, and preparing the suspension liquid.

Thereafter, the suspension liquid was transferred to a 300 mL, a 4-neck flask equipped with a stirrer, a reflux condenser, a thermometer, and a nitrogen inlet tube, and subjected to suspension polymerization for three hours under nitrogen gas current, while stirring and increasing the temperature to 70° C.

Thereafter, interfacial polymerization was conducted. To be specific, an aqueous solution of diethylene triamine in which 1.8 g of diethylene triamine was diluted in 25 g of ion-exchange water was added to the above-described suspension liquid, and the temperature of the suspension liquid was increased to 75° C., and then kept at 75° C.

After elapse of 4 hours from the start of interfacial polymerization, the suspension liquid after the reaction was cooled to 30° C. or less.

The Suspension liquid (suspension formulation) of controlled release particles including a core containing IPBC, and a shell covering the core was obtained in this manner.

Example 10

(Formulation of Suspension Formulation Including OIT-Containing Controlled Release Particles)
(Interfacial Polymerization is Started after the Start of Suspension Polymerization)

A 200 mL beaker (1) was charged with 25 g of OIT, 36 g of methyl methacrylate, 6.0 g of methacrylic acid, 18 g of ethylene glycol dimethacrylate, 15 g of T-1890, and 300 mg of dilauroyl peroxide, and then the mixture was stirred at room temperature, thereby preparing a homogeneous hydrophobic solution.

Separately, a 500 mL beaker (2) was charged with 82.7 g of ion-exchange water, 40 g of a solution of 10 mass % PVA-217 in water, and 200 mg of a solution of 5 mass % DBN in water, and then the mixture was stirred at room temperature, thereby producing a homogeneous aqueous solution.

Then, the hydrophobic solution was added to the 500 mL beaker (2), and the mixture was stirred with T.K. Homo Mixer MARK Model 2.5 (manufactured by PRIMIX Corporation) at a number of revolution of 3500 rpm for 10 min, thereby suspending the hydrophobic solution, and preparing the suspension liquid.

Thereafter, the suspension liquid was transferred to a 300 mL, a 4-neck flask equipped with a stirrer, a reflux condenser, a thermometer, and a nitrogen inlet tube, and subjected to suspension polymerization for three hours under nitrogen gas current, while stirring and increasing the temperature to 70 C. Thereafter, interfacial polymerization was conducted.

To be specific, an aqueous solution of diethylene triamine in which 1.8 g of diethylene triamine was diluted in 25 g of ion-exchange water was added to the suspension liquid, and the temperature of the suspension liquid was increased to 75° C., and then kept at 75° C.

After elapse of 4 hours from the start of interfacial polymerization, the suspension liquid after the reaction was cooled to 30° C. or less.

The suspension liquid (suspension formulation) of controlled release particles including a core containing OIT, and a shell covering the core was obtained in this manner.

Example 11

(Formulation of Suspension Formulation Including Propiconazole-Containing Controlled Release Particles)
(Interfacial Polymerization is Started after the Start of Suspension Polymerization)

A suspension liquid (suspension formulation) of controlled release particles including a core containing Propiconazole and a shell covering the core was produced in the same manner as in Example 9 by sequentially conducting suspension polymerization and interfacial polymerization, except that in the hydrophobic solution, 25 g of Propiconazole was charged instead of 25 g of IPBC, and in the aqueous solution, 40 g of a solution of 10 mass % PVA-217 in water, and 200 mg of a solution of 5 mass % DBN in water were charged instead of 40 g of TCP-10U and 200 mg of an aqueous solution of 5% Pelex SS-L.

Example 12

(Formulation of Suspension Formulation Including Flusilazole-Containing Controlled Release Particles)
(Interfacial Polymerization is Started after the Start of Suspension Polymerization)

A suspension liquid (suspension formulation) of controlled release particles including a core containing Flusilazole and a shell covering the core was produced by sequentially conducting suspension polymerization and interfacial polymerization in the same manner as in Example 11, except that in the hydrophobic solution, 25 g of Flusilazole was charged instead of 25 g of Propiconazole.

Example 13

(Formulation of Suspension Formulation Including Prochloraz-Containing Controlled Release Particles)
(Interfacial Polymerization is Started after the Start of Suspension Polymerization)

A suspension liquid (suspension formulation) of controlled release particles including a core containing prochloraz and a shell covering the core was produced by sequentially conducting suspension polymerization and interfacial polymerization in the same manner as in Example 11, except that in the hydrophobic solution, 25 g of prochloraz was charged instead of 25 g of Propiconazole.

Example 14

(Formulation of Suspension Formulation Including Cyfluthrin-Containing Controlled Release Particles)
(Interfacial Polymerization is Started after the Start of Suspension Polymerization)

A suspension liquid (suspension formulation) of controlled release particles including a core containing cyfluthrin and a shell covering the core was produced by sequentially conducting suspension polymerization and interfacial polymerization in the same manner as in Example 11, except that in the hydrophobic solution, 25 g of cyfluthrin was charged instead of 25 g of Propiconazole.

Comparative Example 1

(Formulation of Suspension Formulation Including IPBC-Containing Controlled Release Particles)
(Suspension Polymerization is Started after the Start of Interfacial Polymerization)

The order of the suspension polymerization and the interfacial polymerization in Example 2 was reversed. That is, a suspension liquid (suspension formulation) of controlled release particles containing IPBC was produced in the same manner as in Example 2, except that, first, interfacial polymerization was conducted, and thereafter, suspension polymerization was conducted.

To be specific, the suspension liquid prepared in the same manner as in Example 2 was transferred to a 500 mL, 4-neck flask equipped with a stirrer, a reflux condenser, a thermometer, and a nitrogen inlet tube, and the temperature was increased under an air atmosphere while stirring.

Under an air atmosphere, when the temperature of the suspension liquid reached 50° C., an aqueous solution of diethylene triamine in which 1.8 g of diethylene triamine was diluted in 25 g of ion-exchange water was added to the suspension liquid, and then the temperature of the suspension liquid was kept at 50° C. for 4 hours, thereby conducting interfacial polymerization. After elapse of 4 hours from the start of interfacial polymerization, absorption of the isocyanate group of T1890 disappeared in infrared absorption spectrum, and completion of interfacial polymerization was confirmed. It was confirmed that at 50° C., with the above-described formulation, the induction period was long, and therefore the suspension polymerization did not start substantially.

Thereafter, under nitrogen gas current, the temperature of the suspension liquid was increased to 75° C. and suspension polymerization was conducted for 4 hours. The suspension liquid after the reaction was cooled to 30° C. or less, thereby producing a suspension liquid (suspension formulation) of controlled release particles containing IPBC.

The obtained suspension liquid was stained with pink color.

Comparative Example 2

(Formulation of Suspension Formulation Including IPBC-Containing Controlled Release Particles)
(Suspension Polymerization was Started after Start of Interfacial Polymerization)

The order of the suspension polymerization and the interfacial polymerization in Example 2 was reversed. That is, a suspension liquid (suspension formulation) of controlled release particles containing IPBC was produced in the same manner as in Example 2 except that first, interfacial polymerization was conducted, and thereafter, suspension polymerization was conducted, and furthermore, interfacial polymerization was conducted at low temperature (38° C.).

To be specific, a 200 mL beaker (1) was charged with 40 g of IPBC, 35 g of methyl methacrylate, 13.5 g of ethylene glycol dimethacrylate, 15 g of T-1890, 300 mg of dilauroyl peroxide, and 20 mg of dibutyltin dilaurate; and then the mixture was stirred at room temperature, thereby preparing a homogeneous hydrophobic solution.

Separately, a 500 mL beaker (2) was charged with 260 g of ion-exchange water, 40 g of a solution of 10 mass % PVA-217 in water, and 200 mg of an aqueous solution of 5% DBN, and then the mixture was stirred at room temperature, thereby producing a homogeneous aqueous solution.

Then, the hydrophobic solution was added to the 500 mL beaker (2), and the mixture was stirred with T.K.Homo Mixer MARK Model 2.5 (manufactured by PRIMIX Corporation) at a number of revolution of 3000 rpm for 10 min, thereby suspending the hydrophobic solution, and preparing the suspension liquid.

Thereafter, the suspension liquid was transferred to a 500 mL, 4-neck flask equipped with a stirrer, a reflux condenser, a thermometer, and a nitrogen inlet tube. The temperature of the suspension liquid was increased while stirring, and interfacial polymerization, and thereafter, the suspension polymerization were conducted.

To be specific, under an air atmosphere, the temperature of the suspension liquid was increased to 38° C., and generation of bubbles of carbon dioxide due to decarboxylation-urea formation (chain extension reaction) between the isocyanate group of T-1890 and water was observed: interfacial polymerization was started. It was confirmed that at 38° C., with the above-described formulation, the suspension polymerization did not start substantially within 5 hours.

Subsequently, the temperature of the suspension liquid was kept at 38° C., and after elapse of 5 hours from the start of interfacial polymerization, absorption of the isocyanate group disappeared in infrared absorption spectrum, and completion of interfacial polymerization was confirmed.

Thereafter, under nitrogen gas current, the temperature of the suspension liquid was increased to 75° C., and suspension polymerization was conducted for 4 hours. Thereafter, the suspension liquid after the reaction was cooled to 30° C. or less, thereby producing a suspension liquid (suspension formulation) of controlled release particles containing IPBC.

Comparative Example 3

(Formulation of Suspension Formulation Including OIT-Containing Controlled Release Particles)
(Suspension Polymerization was Started after Start of Interfacial Polymerization)

The order of the suspension polymerization and the interfacial polymerization in Example 8 was reversed. That is, a suspension liquid (suspension formulation) of controlled release particles containing OIT was produced in the same manner as in Example 8, except that first, suspension polymerization was conducted, and thereafter, interfacial polymerization was conducted.

To be specific, the suspension liquid prepared in the same manner as in Example 8 was transferred to a 500 mL, 4-neck flask equipped with a stirrer, a reflux condenser, a thermometer, and a nitrogen inlet tube, and the temperature was increased while stirring, thereby conducting interfacial polymerization, and then thereafter conducting suspension polymerization.

To be more specific, under an air atmosphere, the temperature of the suspension liquid was increased to 50° C., and an aqueous solution of diethylene triamine in which 1.8 g of diethylene triamine was diluted in 25 g of ion-exchange water was added to the suspension liquid, thereby starting interfacial polymerization.

To be specific, under an air atmosphere, the temperature of the suspension liquid was increased to 50° C., and generation of bubbles of carbon dioxide due to decarboxylation-urea formation (chain extension reaction) between the isocyanate group of T-1890 and water was observed: interfacial polymerization was started. It was confirmed that at 50° C., with the above-described formulation, the suspension polymerization did not substantially start within 4 hours.

Subsequently, the temperature of the suspension liquid was kept at 50° C., and after elapse of 4 hours from the start of interfacial polymerization, absorption of the isocyanate group disappeared in infrared absorption spectrum, and completion of interfacial polymerization was confirmed.

Thereafter, under nitrogen gas current, the temperature of the suspension liquid was increased to 75° C., and suspension polymerization was conducted for 4 hours. Thereafter, the suspension liquid after the reaction was cooled to 30° C. or less, thereby producing a suspension liquid (suspension formulation) of controlled release particles containing IPBC.

Comparative Example 4

(Formulation of Suspension Formulation Including IPBC-Containing Controlled Release Particles)
(Suspension Polymerization)

A 200 mL beaker (1) was charged with 40 g of IPBC, 42 g of methyl methacrylate, 18 g of ethylene glycol dimethacrylate, and 300 mg of dilauroyl peroxide, and then the mixture was stirred at room temperature, thereby preparing a homogeneous hydrophobic solution.

Separately, a 500 mL beaker (2) was charged with 280 g of ion-exchange water, 20 g of an aqueous solution of 10 mass % PVA-217, and 200 mg of a solution of 5 mass % DBN in water, and then the mixture was stirred at room temperature, thereby producing a homogeneous aqueous solution.

Then, the hydrophobic solution was added to the 500 mL beaker (2), and the mixture was stirred with T.K.Homo Mixer MARK Model 2.5 (manufactured by PRIMIX Corporation) at a number of revolution of 3000 rpm for 10 min, thereby suspending the hydrophobic solution, and preparing the suspension liquid.

Thereafter, the suspension liquid was transferred to a 500 mL, 4-neck flask equipped with a stirrer, a reflux condenser, a thermometer, and a nitrogen inlet tube, and subjected to suspension polymerization for six hours under nitrogen gas current, while stirring and increasing the temperature.

To be specific, the suspension polymerization was conducted by increasing the temperature of the suspension liquid to 60° C., keeping it for 1 hour, and then subsequently increasing to 70° C., keeping it for 3 hours, thereafter, increasing to 80° C., and then keeping it for 2 hours.

The suspension liquid after the reaction was cooled to 30° C. or less, thereby producing a suspension liquid (suspension formulation) of controlled release particles containing IPBC.

Comparative Example 5

(Formulation of Suspension Formulation Including Off-Containing Controlled Release Particles)
(Suspension Polymerization)

A 200 mL beaker (1) was charged with 40 g of OIT, 36 g of methyl methacrylate, 6.0 g of methacrylic acid, 18 g of ethylene glycol dimethacrylate, and 300 mg of dilauroyl peroxide, and then the mixture was stirred at room temperature, thereby preparing a homogeneous hydrophobic solution.

Separately, a 500 mL beaker (2) was charged with 280 g of ion-exchange water, 20 g of TCP-10U, and 200 mg of an aqueous solution of 5 mass % Pelex SS-L, and the mixture was stirred at room temperature, thereby producing a homogenous suspension liquid.

Then, the hydrophobic solution was added to the 500 mL beaker (2), and the mixture was stirred with T.K.Homo Mixer MARK Model 2.5 (manufactured by PRIMIX Corporation) at a number of revolution of 3000 rpm for 10 min, thereby suspending the hydrophobic solution, and preparing the suspension liquid.

Thereafter, the suspension liquid was transferred to a 500 mL, 4-neck flask equipped with a stirrer, a reflux condenser, a thermometer, and a nitrogen inlet tube, and subjected to suspension polymerization for six hours under nitrogen gas current, while stirring and increasing the temperature.

To be specific, the suspension polymerization was conducted by increasing the temperature of the suspension liquid to 60° C., keeping it for 1 hour, and then subsequently increasing to 70° C., keeping it for 3 hours, thereafter, increasing to 80° C., and then keeping it for 2 hours.

The suspension liquid after the reaction was cooled to 30° C. or less, thereby producing a suspension liquid (suspension formulation) of controlled release particles containing OIT.

Comparative Example 6

(Formulation of Suspension Formulation Including IPBC-Containing Controlled Release Particles)
(Suspension Polymerization)

A 200 mL beaker (1) was charged with 25 g of IPBC, 52.5 g of methyl methacrylate, 22.5 g of ethylene glycol dimethacrylate, and 300 mg of dilauroyl peroxide, and then the mixture was stirred at room temperature, thereby preparing a homogeneous hydrophobic solution.

Separately, a 500 mL beaker (2) was charged with 109.5 g of ion-exchange water, 40 g of TCP-10U, and 200 mg of an aqueous solution of 5 mass % Pelex SS-L, and the mixture was stirred at room temperature, thereby producing a homogenous suspension liquid.

Then, the hydrophobic solution was added to the 500 mL beaker (2), and the mixture was stirred with T.K. Homo Mixer MARK Model 2.5 (manufactured by PRIMIX Corporation) at a number of revolution of 3500 rpm for 10 min, thereby suspending the hydrophobic solution, and preparing the suspension liquid.

Thereafter, the suspension liquid was transferred to a 300 mL, a 4-neck flask equipped with a stirrer, a reflux condenser, a thermometer, and a nitrogen inlet tube, and subjected to suspension polymerization for six hours under nitrogen gas current, while stirring and increasing the temperature.

To be specific, the suspension polymerization was conducted by increasing the temperature of the suspension liquid to 60° C., keeping it for 1 hour, and then subsequently increasing to 70° C., keeping it for 3 hours, thereafter, increasing to 80° C., and then keeping it for 2 hours.

The suspension liquid after the reaction was cooled to 30° C. or less, thereby producing a suspension liquid (suspension formulation) of controlled release particles containing IPBC.

Comparative Example 7

(Formulation of Suspension Formulation Including OIT-Containing Controlled Release Particles)
(Suspension Polymerization)

A 200 mL beaker (1) was charged with 25 g of OIT, 45 g of methyl methacrylate, 7.5 g of methacrylic acid, 22.5 g of ethylene glycol dimethacrylate, and 300 mg of dilauroyl peroxide, and then the mixture was stirred at room temperature, thereby preparing a homogeneous hydrophobic solution.

Separately, a 500 mL beaker (2) was charged with 109.5 g of ion-exchange water, 40 g of a solution of 10 mass % PVA-217 in water, and 200 mg of a solution of 5 mass % DBN in water, and then the mixture was stirred at room temperature, thereby producing a homogeneous aqueous solution.

Then, the hydrophobic solution was added to the 500 mL beaker (2), and the mixture was stirred with T.K.Homo Mixer MARK Model 2.5 (manufactured by PRIMIX Corporation) at a number of revolution of 3000 rpm for 10 min, thereby suspending the hydrophobic solution, and preparing the suspension liquid.

Thereafter, the suspension liquid was transferred to a 300 mL, a 4-neck flask equipped with a stirrer, a reflux condenser, a thermometer, and a nitrogen inlet tube, and subjected to suspension polymerization for six hours under nitrogen gas current, while stirring and increasing the temperature.

To be specific, the suspension polymerization was conducted by increasing the temperature of the suspension liquid to 60° C., keeping it for 1 hour, and then subsequently increasing to 70° C., keeping it for 3 hours, thereafter, increasing to 80° C., and then keeping it for 2 hours.

The suspension liquid after the reaction was cooled to 30° C. or less, thereby producing a suspension liquid (suspension formulation) of controlled release particles containing OIT.

Comparative Example 8

(Formulation of Suspension Formulation Including Propiconazole-Containing Controlled Release Particles)
(Suspension Polymerization)

A suspension liquid (suspension formulation) of controlled release particles containing Propiconazole was produced by conducting suspension polymerization in the same manner as in Comparative Example 6, except that in the hydrophobic solution, 25 g of Propiconazole was charged instead of 25 g of IPBC, and in the aqueous solution, 40 g of a solution of 10 mass % PVA-217 in water, and 200 mg of a solution of 5 mass % DBN in water were charged instead of 40 g of TCP-10U and 200 mg of an aqueous solution of 5% Pelex SS-L.

Comparative Example 9

(Formulation of Suspension Formulation Including Flusilazole-Containing Controlled Release Particles)
(Suspension Polymerization)

A suspension liquid (suspension formulation) of controlled release particles containing Flusilazole was produced by conducting suspension polymerization in the same manner as in Comparative Example 8, except that in the hydrophobic solution, 25 g of Flusilazole was charged instead of 25 g of Propiconazole.

Comparative Example 10

(Formulation of Suspension Formulation Including Prochloraz-Containing Controlled Release Particles)
(Suspension Polymerization)

A suspension liquid (suspension formulation) of controlled release particles containing prochloraz was produced by conducting suspension polymerization in the same manner as in Comparative Example 8, except that in the hydrophobic solution, 25 g of prochloraz was charged instead of 25 g of Propiconazole.

Comparative Example 11

(Formulation of Suspension Formulation Including Cyfluthrin-Containing Controlled Release Particles)
(Suspension Polymerization)

A suspension liquid (suspension formulation) of controlled release particles containing cyfluthrin was produced by conducting suspension polymerization in the same manner as in Comparative Example 8, except that in the hydrophobic solution, 25 g of cyfluthrin was charged instead of 25 g of Propiconazole.

(Mixing Formulation)

Formulation of components in Examples and Comparative Examples is shown in Table 2 to Table 6. In the tables, values of the mixing formulation are shown in grams.

TABLE 2

| | | | | Molecular Weight | Melting Point (° C.) | Example 1 | Example 2 | Example 3 | Example 4 | Example 5 |
|---|---|---|---|---|---|---|---|---|---|---|
| Hydrophobic Solution | First Component | Antibiotic Compound | IPBC | 281 | 60 | 40 | 40 | 40 | 45 | 40 |
| | | | OIT | 213 | <20 | — | — | — | — | — |
| | | | Propiconazole | 342 | <20 | — | — | — | — | — |
| | | | Flusilazole | 315 | 54 | — | — | — | — | — |
| | | | Prochloraz | 375 | 45 to 52 | — | — | — | — | — |
| | | | Cyfluthrin | 434 | 57, 74, 66*[1] | — | — | — | — | — |
| | | Ratio of Antibiotic Compound to Polymerizable Vinyl Monomer | | | | 0.80 | 0.89 | 1.00 | 1.125 | 0.89 |
| | | Solubility Parameter δ [(J/cm$^3$)$^{1/2}$] | | Polar Term $\delta_{p,\,compound}$ | | 3.23 | 3.23 | 3.23 | 3.23 | 3.23 |
| | | | | Hydrogen Bonding Term $\delta_{h,\,compound}$ | | 7.83 | 7.83 | 7.83 | 7.83 | 7.83 |
| | Polymerizable Vinyl Monomer | Miscible Monomer | Methyl Methacrylate | | | 35 | 31.5 | 28 | 28 | 31.5 |
| | | | Methacrylic Acid | | | — | — | — | — | — |
| | | Crosslinkable Monomer | Ethylene Glycol Dimethacrylate | | | 15 | 13.5 | 12 | 12 | 13.5 |
| | Second Component | Polyisocyanate Component*[2] | | T1890 | | 10 | 15 | 20 | 15 | 15 |
| | | Initiator | | Dilauroyl Peroxide | | 0.3 | 0.3 | 0.3 | 0.3 | 0.3 |

TABLE 2-continued

| | | | Molecular Weight | Melting Point (° C.) | Example 1 | Example 2 | Example 3 | Example 4 | Example 5 |
|---|---|---|---|---|---|---|---|---|---|
| | Ratio of Polyisocyanate Component to Polymerizable Vinyl Monomer | | | | 0.2 | 0.33 | 0.5 | 0.38 | 0.33 |
| | Polyaddition Catalyst | | Dibutyltin Dilaurate | | — | — | — | — | — |
| | Polymer | Solubility Parameter $\delta$ [(J/cm$^3$)$^{1/2}$] | Polar Term $\delta_{p.\,polymer}$ | | 5.80 | 5.80 | 5.80 | 5.80 | 5.80 |
| | | | Hydrogen Bonding Term $\delta_{h.\,polymer}$ | | 9.60 | 9.60 | 9.60 | 9.60 | 9.60 |
| | Ion-exchange Water | | | | 233 | 233 | 233 | 133 | 233 |
| | Dispersing Agent | | PVA-217 (10%) | | 40 | 40 | 40 | 40 | 40 |
| | | | TCP-10U | | — | — | — | — | — |
| | Surfactant | | DBN (5%) | | 0.2 | 0.2 | 0.2 | 0.2 | 0.2 |
| | | | Pelex SS-L (5%) | | — | — | — | — | — |
| Second Component | Active Hydrogen Group-containing Compound*$^3$ | | Diethylene Triamine | | 1.2 | 1.8 | 2.4 | 1.8 | 1.8 |
| | Dilution Water (Ion-exchange Water) | | | | 25 | 25 | 25 | 25 | 25 |
| $\Delta\delta_p$ | (=$\delta_{p.\,polymer} - \delta_{p.\,compound}$)[J/cm$^3$]$^{1/2}$ | | | | 2.57 | 2.57 | 2.57 | 2.57 | 2.57 |
| $\Delta\delta_h$ | (=$\delta_{h.\,polymer} - \delta_{h.\,compound}$)[J/cm$^3$]$^{1/2}$ | | | | 1.77 | 1.77 | 1.77 | 1.77 | 1.77 |
| | First Step (Polymerization Time) | | | | Suspension Polymerization (3 Hr) | Suspension Polymerization (3 Hr) | Suspension Polymerization (3 Hr) | Suspension Polymerization (3 Hr) | Suspension Polymerization (2 Hr) |
| | Second Step (Polymerization Time) | | | | Interfacial Polymerization (4 Hr) | Interfacial Polymerization (4 Hr) | Interfacial Polymerization (4 Hr) | Interfacial Polymerization (4 Hr) | Interfacial Polymerization (4 Hr) |
| | Controlled Release Particle Concentration(wt %) [vs Suspension Liquid] | | | | 26.4 | 26.5 | 26.7 | 35.3 | 26.5 |
| | Antibiotic Compound Concentration(wt %) [vs Suspension Liquid] | | | | 10.0 | 10.0 | 10.0 | 15.0 | 10.0 |
| | Homo Mixer Stirring Conditions for Suspension | | Number of Revolution (rpm) | | 3000 | 3000 | 3000 | 4000 | 3000 |
| | Median Size of Controlled Release Particles (μm) | | | | 13 | 15 | 18 | 7.5 | 16 |

*$^1$Including Isomer IV (Melting Point 102° C.)
*$^2$First Shell-forming Component
*$^3$Second Shell-forming Component

TABLE 3

| | | | | Molecular Weight | Melting Point (° C.) | Example 6 | Example 7 | Example 8 |
|---|---|---|---|---|---|---|---|---|
| Hydrophobic Solution | First Component | Antibiotic Compound | IPBC | 281 | 60 | 40 | 40 | — |
| | | | OIT | 213 | <20 | — | — | 40 |
| | | | Propiconazole | 342 | <20 | — | — | — |
| | | | Flusilazole | 315 | 54 | — | — | — |
| | | | Prochloraz | 375 | 45 to 52 | — | — | — |
| | | | Cyfluthrin | 434 | 57, 74, 66*$^1$ | — | — | — |
| | | Ratio of Antibiotic Compound to Polymerizable Vinyl Monomer | | | | 0.89 | 0.89 | 0.89 |
| | | Solubility Parameter $\delta$ [(J/cm$^3$)$^{1/2}$] | Polar Term $\delta_{p.\,compound}$ | | | 3.23 | 3.23 | 5.47 |
| | | | Hydrogen Bonding Term $\delta_{h.\,compound}$ | | | 7.83 | 7.83 | 5.87 |
| | | Polymerizable Vinyl Monomer | Miscible Monomer | Methyl Methacrylate | | 31.5 | 31.5 | 27 |
| | | | | Methacrylic Acid | | — | — | 4.5 |
| | | | Crosslinkable Monomer | Ethylene Glycol Dimethacrylate | | 13.5 | 13.5 | 13.5 |
| | Second Component | Polyisocyanate Component*$^2$ | T1890 | | | 15 | 15 | 15 |
| | | Initiator | Dilauroyl Peroxide | | | 0.3 | 0.3 | 0.3 |
| | Ratio of Polyisocyanate Component to Polymerizable Vinyl Monomer | | | | | 0.33 | 0.33 | 0.33 |
| | Polyaddition Catalyst | | Dibutyltin Dilaurate | | | — | — | — |
| | Polymer | Solubility Parameter $\delta$ [(J/cm$^3$)$^{1/2}$] | Polar Term $\delta_{p.\,polymer}$ | | | 5.80 | 5.80 | 5.91 |
| | | | Hydrogen Bonding Term $\delta_{h.\,polymer}$ | | | 9.60 | 9.60 | 9.98 |
| | Ion-exchange Water | | | | | 233 | 233 | 230 |
| | Dispersing Agent | | PVA-217 (10%) | | | 40 | — | — |
| | | | TCP-10U | | | — | 40 | 40 |
| | Surfactant | | DBN (5%) | | | 0.2 | — | — |
| | | | Pelex SS-L (5%) | | | — | 0.2 | 0.2 |
| Second Component | Active Hydrogen Group-containing Compound*$^3$ | | Diethylene Triamine | | | 1.8 | 1.8 | 1.8 |
| | Dilution Water (Ion-exchange Water) | | | | | 25 | 25 | 25 |
| $\Delta\delta_p$ | (=$\delta_{p.\,polymer} - \delta_{p.\,compound}$)[J/cm$^3$]$^{1/2}$ | | | | | 2.57 | 2.57 | 0.44 |
| $\Delta\delta_h$ | (=$\delta_{h.\,polymer} - \delta_{h.\,compound}$)[J/cm$^3$]$^{1/2}$ | | | | | 1.77 | 1.77 | 4.11 |
| | First Step (Polymerization Time) | | | | | Interfacial | Suspension | Suspension |

TABLE 3-continued

|  |  |  |  |  |  | Second Step (Polymerization Time) | Polymerization/ Suspension Polymerization Simultaneous Start (7 Hr) | Polymerization (3 Hr) Interfacial Polymerization (4 Hr) | Polymerization (3 Hr) Interfacial Polymerization (4 Hr) |
|---|---|---|---|---|---|---|---|---|---|
|  |  |  |  |  |  | Controlled Release Particle Concentration (wt %) [vs Suspension Liquid] | 26.5 | 26.5 | 26.5 |
|  |  |  |  |  |  | Antibiotic Compound Concentration (wt %) [vs Suspension Liquid] | 10.0 | 10.0 | 10.0 |
|  |  |  |  |  |  | Homo Mixer Stirring Conditions for Suspension  Number of Revolution(rpm) | 3000 | 3000 | 3000 |
|  |  |  |  |  |  | Median Size of Controlled Release Particles (μm) | 17 | 21 | 19 |

|  |  |  |  |  | Molecular Weight | Melting Point (° C.) | Example 9 | Example 10 |
|---|---|---|---|---|---|---|---|---|
| Hydrophobic Solution | First Component | Antibiotic Compound | IPBC | | 281 | 60 | 25 | — |
|  |  |  | OIT | | 213 | <20 | — | 25 |
|  |  |  | Propiconazole | | 342 | <20 | — | — |
|  |  |  | Flusilazole | | 315 | 54 | — | — |
|  |  |  | Prochloraz | | 375 | 45 to 52 | — | — |
|  |  |  | Cyfluthrin | | 434 | 57, 74, 66*[1] | — | — |
|  |  | Ratio of Antibiotic Compound to Polymerizable Vinyl Monomer | | | | | 0.42 | 0.42 |
|  |  | Solubility Parameter δ $[(J/cm^3)^{1/2}]$ | Polar Term $\delta_{p.\ compound}$ | | | | 3.23 | 5.47 |
|  |  |  | Hydrogen Bonding Term $\delta_{h.\ compound}$ | | | | 7.83 | 5.87 |
|  | Polymerizable Vinyl Monomer | Miscible Monomer | Methyl Methacrylate | | | | 50 | 36 |
|  |  |  | Methacrylic Acid | | | | — | 6.0 |
|  |  | Crosslinkable Monomer | Ethylene Glycol Dimethacrylate | | | | 10 | 18 |
|  | Second Component | Polyisocyanate Component*[2] | T1890 | | | | 15 | 15 |
|  |  | Initiator | Dilauroyl Peroxide | | | | 0.3 | 0.3 |
|  |  | Ratio of Polyisocyanate Component to Polymerizable Vinyl Monomer | | | | | 0.25 | 0.25 |
|  |  | Polyaddition Catalyst | Dibutyltin Dilaurate | | | | — | — |
|  | Polymer | Solubility Parameter δ $[(J/cm^3)^{1/2}]$ | Polar Term $\delta_{p.\ polymer}$ | | | | 5.88 | 5.91 |
|  |  |  | Hydrogen Bonding Term $\delta_{h.\ polymer}$ | | | | 9.44 | 9.98 |
| Ion-exchange Water |  |  |  | | | | 82.7 | 82.7 |
| Dispersing Agent |  |  | PVA-217 (10%) | | | | — | 40 |
|  |  |  | TCP-10U | | | | 40 | — |
| Surfactant |  |  | DBN (5%) | | | | — | 0.2 |
|  |  |  | Pelex SS-L (5%) | | | | 0.2 | — |
| Second Component |  | Active Hydrogen Group-containing Compound*[3] | Diethylene Triamine | | | | 1.8 | 1.8 |
|  |  | Dilution Water (Ion-exchange Water) | | | | | 25 | 25 |
| $\Delta\delta_p$ |  | $(=\delta_{p.\ polymer} - \delta_{p.\ compound})[J/cm^3]^{1/2}$ | | | | | 2.65 | 0.44 |
| $\Delta\delta_h$ |  | $(=\delta_{h.\ polymer} - \delta_{h.\ compound})[J/cm^3]^{1/2}$ | | | | | 1.61 | 4.11 |
| First Step (Polymerization Time) |  |  |  | | | | Suspension Polymerization (3 Hr) | Suspension Polymerization (3 Hr) |
| Second Step (Polymerization Time) |  |  |  | | | | Interfacial Polymerization (4 Hr) | Interfacial Polymerization (4 Hr) |
| Controlled Release Particle Concentration (wt %) [vs Suspension Liquid] |  |  |  | | | | 42.4 | 42.4 |
| Antibiotic Compound Concentration (wt %) [vs Suspension Liquid] |  |  |  | | | | 10.0 | 10.0 |
| Homo Mixer Stirring Conditions for Suspension  Number of Revolution(rpm) |  |  |  | | | | 4000 | 3500 |
| Median Size of Controlled Release Particles (μm) |  |  |  | | | | 19 | 10 |

*[1]Including Isomer IV (Melting Point 102° C.)
*[2]First Shell-forming Component
*[3]Second Shell-forming Component

TABLE 4

|  |  |  |  | Molecular Weight | Melting Point (° C.) | Example 11 | Example 12 | Example 13 | Example 14 | Comp. Ex. 1 |
|---|---|---|---|---|---|---|---|---|---|---|
| Hydrophobic Solution | First Component | Antibiotic Compound | IPBC | 281 | 60 | — | — | — | — | 40 |
|  |  |  | OIT | 213 | <20 | — | — | — | — | — |
|  |  |  | Propiconazole | 342 | <20 | 25 | — | — | — | — |
|  |  |  | Flusilazole | 315 | 54 | — | 25 | — | — | — |
|  |  |  | Prochloraz | 375 | 45 to 52 | — | — | 25 | — | — |
|  |  |  | Cyfluthrin | 434 | 57, 74, 66*[1] | — | — | — | 25 | — |
|  |  | Ratio of Antibiotic Compound to Polymerizable Vinyl Monomer |  |  |  | 0.42 | 0.42 | 0.42 | 0.42 | 0.89 |
|  |  | Solubility | Polar Term $\delta_{p.\ compound}$ |  |  | 6.55 | 5.95 | 7.07 | 3.46 | 3.23 |

TABLE 4-continued

| | | | Molecular Weight | Melting Point (° C.) | Example 11 | Example 12 | Example 13 | Example 14 | Comp. Ex. 1 |
|---|---|---|---|---|---|---|---|---|---|
| | | Parameter δ $[(J/cm^3)^{1/2}]$ | Hydrogen Bonding Term $\delta_{h.\ compound}$ | | 9.44 | 6.85 | 8.31 | 6.09 | 7.83 |
| | Polymerizable Vinyl Monomer | Miscible Monomer | Methyl Methacrylate | | 50 | 50 | 50 | 50 | 31.5 |
| | | | Methacrylic Acid | | — | — | — | — | — |
| | | Crosslinkable Monomer | Ethylene Glycol Dimethacrylate | | 10 | 10 | 10 | 10 | 13.5 |
| Second Component | Polyisocyanate Component*[2] | | T1890 | | 15 | 15 | 15 | 15 | 15 |
| | Initiator | | Dilauroyl Peroxide | | 0.3 | 0.3 | 0.3 | 0.3 | 0.3 |
| | Ratio of Polyisocyanate Component to Polymerizable Vinyl Monomer | | | | 0.25 | 0.25 | 0.25 | 0.25 | 0.33 |
| | Polyaddition Catalyst | | Dibutyltin Dilaurate | | — | — | — | — | — |
| | Polymer Solubility Parameter δ $[(J/cm^3)^{1/2}]$ | | Polar Term $\delta_{p.\ polymer}$ | | 5.88 | 5.88 | 5.88 | 5.88 | 5.80 |
| | | | Hydrogen Bonding Term $\delta_{h.\ polymer}$ | | 9.44 | 9.44 | 9.44 | 9.44 | 9.60 |
| | Ion-exchange Water | | | | 82.7 | 82.7 | 82.7 | 82.7 | 233 |
| | Dispersing Agent | | PVA-217 (10%) | | 40 | 40 | 40 | 40 | 40 |
| | | | TCP-10U | | — | — | — | — | — |
| | Surfactant | | DBN (5%) | | 0.2 | 0.2 | 0.2 | 0.2 | 0.2 |
| | | | Pelex SS-L (5%) | | — | — | — | — | — |
| Second Component | Active Hydrogen Group-containing Compound*[3] | | Diethylene Triamine | | 1.8 | 1.8 | 1.8 | 1.8 | 1.8 |
| | Dilution Water (Ion-exchange Water) | | | | 25 | 25 | 25 | 25 | 25 |
| $\Delta\delta_p$ | $(=\delta_{p.\ polymer} - \delta_{p.\ compound})[J/cm^3]^{1/2}$ | | | | −0.67 | −0.07 | −0.99 | 2.42 | 2.57 |
| $\Delta\delta_h$ | $(=\delta_{h.\ polymer} - \delta_{h.\ compound})[J/cm^3]^{1/2}$ | | | | 0 | 2.59 | 0.59 | 3.35 | 1.77 |
| | First Step (Polymerization Time) | | | | Suspension Polymerization (3 Hr) | Suspension Polymerization (3 Hr) | Suspension Polymerization (3 Hr) | Suspension Polymerization (3 Hr) | Interfacial Polymerization (4 Hr) |
| | Second Step (Polymerization Time) | | | | Interfacial Polymerization (4 Hr) | Interfacial Polymerization (4 Hr) | Interfacial Polymerization (4 Hr) | Interfacial Polymerization (4 Hr) | Suspension Polymerization (4 Hr) |
| Controlled Release Particle Concentration (wt %) [vs Suspension Liquid] | | | | | 42.4 | 42.4 | 42.4 | 42.4 | 26.5 |
| Antibiotic Compound Concentration (wt %) [vs Suspension Liquid] | | | | | 10.0 | 10.0 | 10.0 | 10.0 | 10.0 |
| Homo Mixer Stirring Conditions for Suspension | | | Number of Revolution (rpm) | | 4000 | 4000 | 4000 | 4000 | 3000 |
| Median Size of Controlled Release Particles (μm) | | | | | 18 | 18 | 17 | 19 | 15 |

*[1]Including Isomer IV (Melting Point 102° C.)
*[2]First Shell-forming Component
*[3]Second Shell-forming Component

TABLE 5

| | | | Molecular Weight | Melting Point (° C.) | Comp. Ex. 2 | Comp. Ex. 3 | Comp. Ex. 4 | Comp. Ex. 5 | Comp. Ex. 6 |
|---|---|---|---|---|---|---|---|---|---|
| Hydrophobic Solution | First Component | Antibiotic Compound | | | | | | | |
| | | IPBC | 281 | 60 | 40 | — | 40 | — | 25 |
| | | OIT | 213 | <20 | — | 40 | — | 40 | — |
| | | Propiconazole | 342 | <20 | — | — | — | — | — |
| | | Flusilazole | 315 | 54 | — | — | — | — | — |
| | | Prochloraz | 375 | 45 to 52 | — | — | — | — | — |
| | | Cyfluthrin | 434 | 57, 74, 66*¹ | — | — | — | — | — |
| | | Ratio of Antibiotic Compound to Polymerizable Vinyl Monomer | | | 0.89 | 0.89 | 0.67 | 0.67 | 0.33 |
| | | Solubility Parameter δ Polar Term δ$_{p,\,compound}$ [(J/cm³)^{1/2}] | | | 3.23 | 5.47 | 3.23 | 5.47 | 3.23 |
| | | Hydrogen Bonding Term δ$_{h,\,compound}$ [(J/cm³)^{1/2}] | | | 7.83 | 5.87 | 7.83 | 5.87 | 7.83 |
| | Polymerizable Vinyl Monomer | Miscible Monomer Methacrylic Acid | | | 31.5 | 27 | 42 | 36 | 52.5 |
| | | Crosslinkable Monomer Ethylene Glycol Dimethacrylate | | | 4.5 | — | 6.0 | — | — |
| | Second Component | Polyisocyanate Component*² T1890 | | | 13.5 | 13.5 | 18 | 18 | 22.5 |
| | | | | | 15 | 15 | — | — | — |
| | | Initiator Dilauroyl Peroxide | | | 0.3 | 0.3 | 0.3 | 0.3 | 0.3 |
| | | Ratio of Polyisocyanate Component to Polymerizable Vinyl Monomer | | | 0.33 | 0.33 | 0 | 0 | 0 |
| | | Polyaddition Catalyst Dibutyltin Dilaurate | | | 0.02 | — | — | — | — |
| | Polymer | Solubility Parameter δ Polar Term δ$_{p,\,polymer}$ [(J/cm³)^{1/2}] | | | 5.80 | 5.91 | 5.80 | 5.91 | 5.80 |
| | | Hydrogen Bonding Term δ$_{h,\,polymer}$ [(J/cm³)^{1/2}] | | | 9.60 | 9.98 | 9.60 | 9.98 | 9.60 |
| | | Ion-exchange Water | | | 260 | 233 | 280 | 280 | 109.5 |
| | Dispersing Agent | PVA-217 (10%) | | | 40 | — | 20 | 20 | 40 |
| | | TCP-10U | | | — | 40 | — | — | — |
| | Surfactant | DBN (5%) | | | 0.2 | 0.2 | 0.2 | 0.2 | 0.2 |
| | | Pelex SS-L (5%) | | | — | 1.8 | — | — | — |
| Second Component | | Active Hydrogen Group-containing Compound*³ Diethylene Triamine | | | — | 25 | — | — | — |
| | | Dilution Water (Ion-exchange Water) | | | 2.57 | 0.44 | 2.57 | 2.57 | 2.57 |
| Δδ$_p$ | | $(=δ_{p,\,polymer} - δ_{p,\,compound})$ [(J/cm³)^{1/2}] | | | 1.77 | 4.11 | 1.77 | 1.77 | 1.77 |
| Δδ$_h$ | | $(=δ_{h,\,polymer} - δ_{h,\,compound})$ [(J/cm³)^{1/2}] | | | | | | | |
| | | First Step (Polymerization Time) | | | Interfacial Polymerization (5 Hr) | Interfacial Polymerization (4 Hr) | Suspension Polymerization (6 Hr) | Suspension Polymerization (6 Hr) | Suspension Polymerization (6 Hr) |
| | | Second Step (Polymerization Time) | | | Suspension Polymerization (4 Hr) | Suspension Polymerization (4 Hr) | — | — | — |
| | | Controlled Release Particle Concentration(wt %) [vs Suspension Liquid] | | | 26.5 | 26.5 | 25.5 | 25.5 | 41.7 |
| | | Antibiotic Compound Concentration(wt %) [vs Suspension Liquid] | | | 10.0 | 10.0 | 10.0 | 10.0 | 10.0 |
| | | Homo Mixer Stirring Conditions for Suspension Number of Revolution (rpm) | | | 3000 | 3000 | 3000 | 3000 | 3500 |
| | | Median Size of Controlled Release Particles (μm) | | | 18 | 20 | 14 | 17 | 18 |

*¹Including Isomer IV (Melting Point 102° C.)
*²First Shell-forming Component
*³Second Shell-forming Component

TABLE 6

| | | | Molecular Weight | Melting Point (° C.) | Comp. Ex. 7 | Comp. Ex. 8 | Comp. Ex. 9 | Comp. Ex. 10 | Comp. Ex. 11 |
|---|---|---|---|---|---|---|---|---|---|
| Hydrophobic Solution | First Component | Antibiotic Compound | | | | | | | |
| | | IPBC | 281 | 60 | 25 | — | — | — | — |
| | | OIT | 213 | <20 | — | 25 | — | — | — |
| | | Propiconazole | 342 | <20 | — | — | 25 | — | — |
| | | Flusilazole | 315 | 54 | — | — | — | 25 | — |
| | | Prochloraz | 375 | 45 to 52 | — | — | — | — | — |
| | | Cyfluthrin | 434 | 57, 74, 66[*1] | — | — | — | — | 25 |
| | | Ratio of Antibiotic Compound to Polymerizable Vinyl Monomer | | | 0.48 | 0.48 | 0.48 | 0.48 | 0.48 |
| | | Solubility Parameter $\delta$ Polar Term $\delta_{p,\,compound}$ $[J/cm^3]^{1/2}$ | | | 5.47 | 6.55 | 5.95 | 7.07 | 3.46 |
| | | Hydrogen Bonding Term $\delta_{h,\,compound}$ $[J/cm^3]^{1/2}$ | | | 5.87 | 9.44 | 6.85 | 8.31 | 6.09 |
| | Polymerizable Vinyl Monomer | Miscible Monomer | | | | | | | |
| | | Methyl Methacrylate | | | 45 | 52.5 | 52.5 | 52.5 | 52.5 |
| | | Methacrylic Acid | | | 7.5 | — | — | — | — |
| | | Crosslinkable Monomer[*2] | | | | | | | |
| | | Ethylene Glycol Dimethacrylate | | | 22.5 | 22.5 | 22.5 | 22.5 | 22.5 |
| | Second Component | Polyisocyanate Component[*2] | | | | | | | |
| | | T1890 | | | — | — | — | — | — |
| | | Initiator | | | | | | | |
| | | Dilauroyl Peroxide | | | 0.3 | 0.3 | 0.3 | 0.3 | 0.3 |
| | | Ratio of Polyisocyanate Component to Polymerizable Vinyl Monomer | | | 0 | 0 | 0 | 0 | 0 |
| | | Polyaddition Catalyst | | | | | | | |
| | | Dilauric Acid | | | — | — | — | — | — |
| | Polymer | Solubility Parameter $\delta$ Polar Term $\delta_{p,\,polymer}$ $[J/cm^3]^{1/2}$ | | | 5.91 | 5.80 | 5.80 | 5.80 | 5.80 |
| | | Hydrogen Bonding Term $\delta_{h,\,polymer}$ $[J/cm^3]^{1/2}$ | | | 9.98 | 9.60 | 9.60 | 9.60 | 9.60 |
| | | Ion-exchange Water | | | 109.5 | 109.5 | 109.5 | 109.5 | 109.5 |
| | Dispersing Agent | PVA-217 (10%) | | | 40 | 40 | 40 | 40 | 40 |
| | | TCP-10U | | | — | — | — | — | — |
| | | DBN (5%) | | | — | — | — | — | — |
| | Surfactant | Pelex SS-L (5%) | | | 0.2 | 0.2 | 0.2 | 0.2 | 0.2 |
| Second Component | Active Hydrogen Group-containing Compound[*3] | | | | | | | | |
| | | Diethylene Triamine | | | — | — | — | — | — |
| | Diluent (Ion-exchange Water) | | | | — | — | — | — | — |
| $\Delta\delta_p$ | | $(=\delta_{p,\,polymer}-\delta_{p,\,compound})\,[J/cm^3]^{1/2}$ | | | | | | | |
| $\Delta\delta_h$ | | $(=\delta_{h,\,polymer}-\delta_{h,\,compound})\,[J/cm^3]^{1/2}$ | | | | | | | |
| | First Step (Polymerization Time) | | | | Suspension Polymerization (6 Hr) | Suspension Polymerization (6 Hr) | Suspension Polymerization (6 Hr) | Suspension Polymerization (6 Hr) | Suspension Polymerization (6 Hr) |
| | Second Step (Polymerization Time) | | | | — | — | — | — | — |
| | Controlled Release Particle Concentration(wt %) [vs Suspension Liquid] | | | | 41.7 | 41.7 | 41.7 | 41.7 | 41.7 |
| | Antibiotic Compound Concentration(wt %) [vs Suspension Liquid] | | | | 10.0 | 10.0 | 10.0 | 10.0 | 10.0 |
| | Homo Mixer Stirring Conditions for Suspension Number of Revolution (rpm) | | | | 3000 | 3000 | 3000 | 3000 | 3000 |
| | Median Size of Controlled Release Particles (μm) | | | | 12 | 16 | 16 | 15 | 19 |

[*1]Including Isomer IV (Melting Point 102° C.)
[*2]First Shell-forming Component
[*3]Second Shell-forming Component (Calculation of Solubility Parameter δ)

1. The polar term $\delta_{p,polymer}$ and the hydrogen bonding term $\delta_{h,polymer}$ of the solubility parameter δ of the polymer of the core was calculated as described above.

Table 2 to Table 6 show the results of calculation along with the polar term $\delta_{p,compound}$ and the hydrogen bonding term $\delta_{h,compound}$ of the solubility parameter δ of the antibiotic compound.

2. $\Delta\delta_p$ ($=\delta_{p,polymer}-\delta_{p,compound}$) and $\Delta\delta h$ ($=\delta_{h,polymer}-\delta_{h,compound}$) were calculated.

The results are shown in Table 2 to Table 6.

Evaluation

1. Median Size

The suspension liquids obtained in Examples and Comparative Examples were measured with a laser diffraction scattering particle size distribution analyzer LA-920 (manufactured by HORIBA, Ltd.), thereby measuring the median size of controlled release particles. The results are shown in Table 2 to Table 6.

2. SEM (Scanning Electron Microscope) Observation

The suspension liquids (suspension formulation) of Examples 1 to 8 and Comparative Examples 1, 2, and 4 that were allowed to stand at room temperature for 5 weeks or more were dropped on a stage, and thereafter, after distilling off water, the obtained controlled release particles were subjected to SEM observation with a scanning electron microscope, Hitachi TM-100 (manufactured by Hitachi High-Technologies Corporation).

FIGS. 1 to 11 show image-processed SEM photograph of Examples 1 to 8 and Comparative Examples 1, 2, and 4, respectively.

As is clear from FIGS. 1 to 5, and 7, other than the controlled release particles of Examples 1 to 5, and 7, no crystal of antibiotic compound (IPBC) is seen. Also as is clear from FIG. 8, other than the controlled release particles of Example 8, no presence of the antibiotic compound (OIT) is seen.

Figure 6:
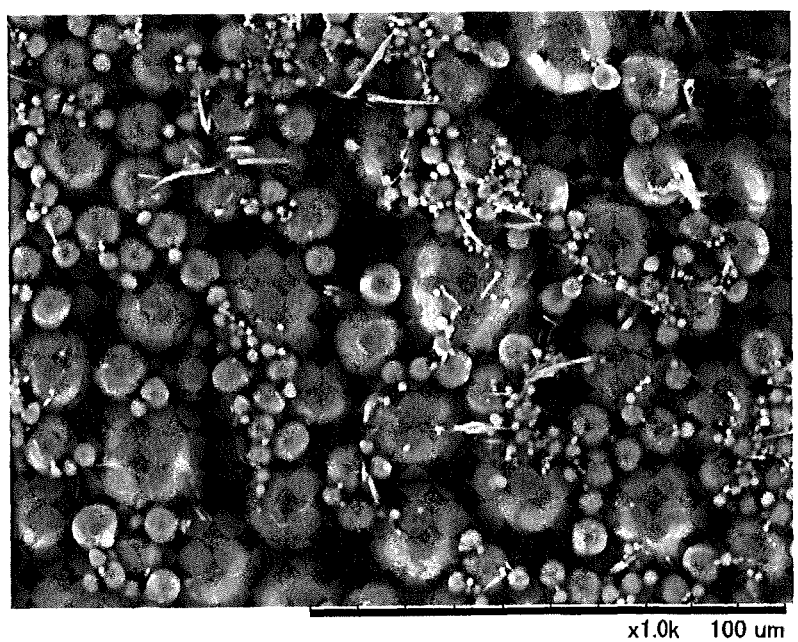
FIG. 6 shows an image-processed SEM photograph of controlled release particles of Example 6.
Figure 7:
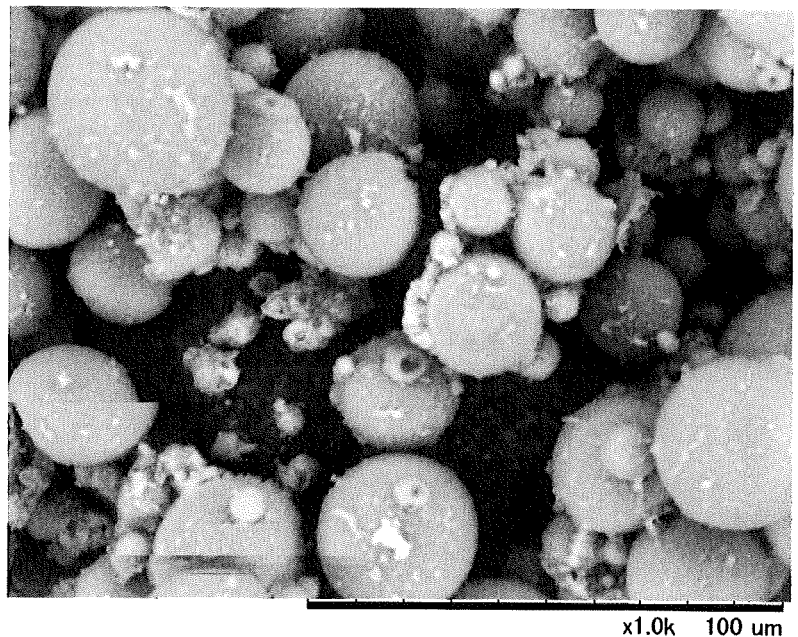
FIG. 7 shows an image-processed SEM photograph of controlled release particles of Example 7.
Figure 8:
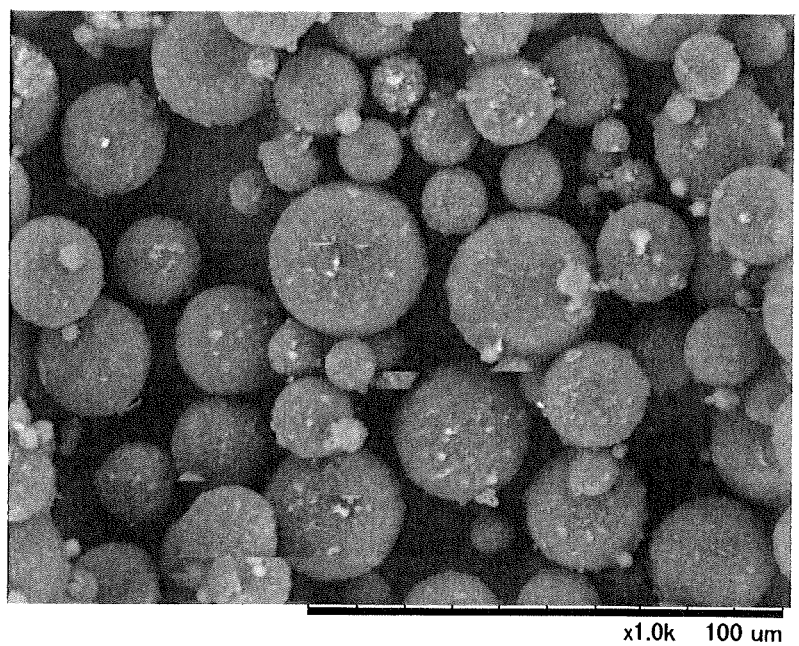
FIG. 8 shows an image-processed SEM photograph of controlled release particles of Example 8.

As is clear from FIG. 6, in addition to the controlled release particles of Example 6, a slight amount of needle crystals of the antibiotic compound (IPBC) is seen.

Figure 9:
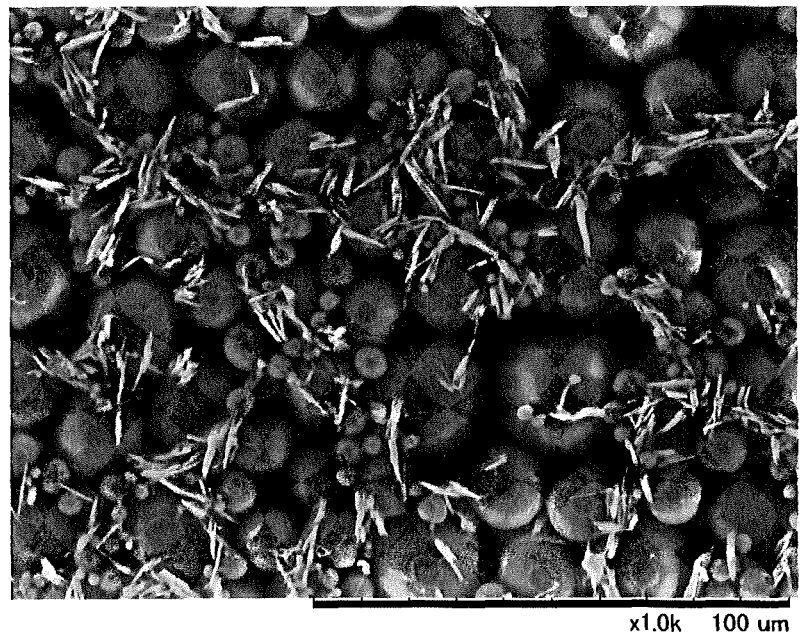
FIG. 9 shows an image-processed SEM photograph of controlled release particles of Comparative Example 1.
Figure 10:
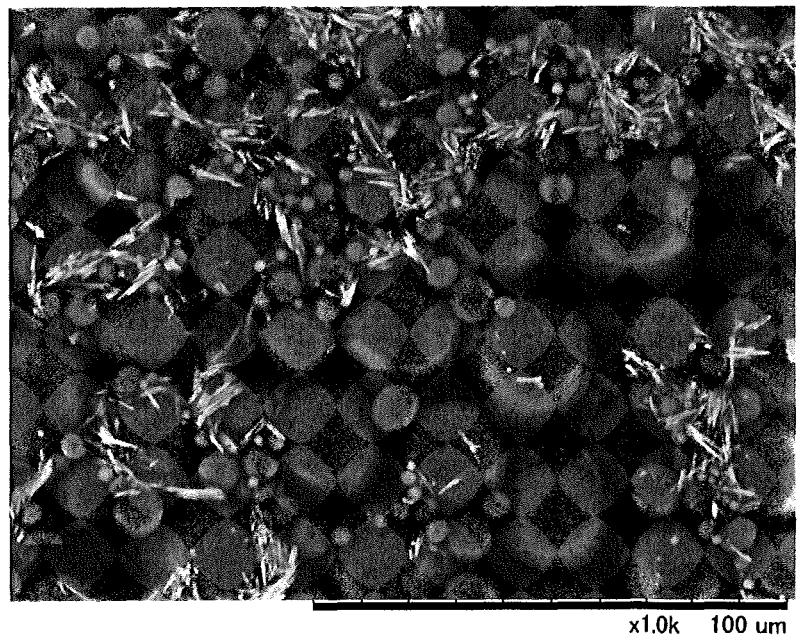
FIG. 10 shows an image-processed SEM photograph of controlled release particles of Comparative Example 2.
Figure 11:
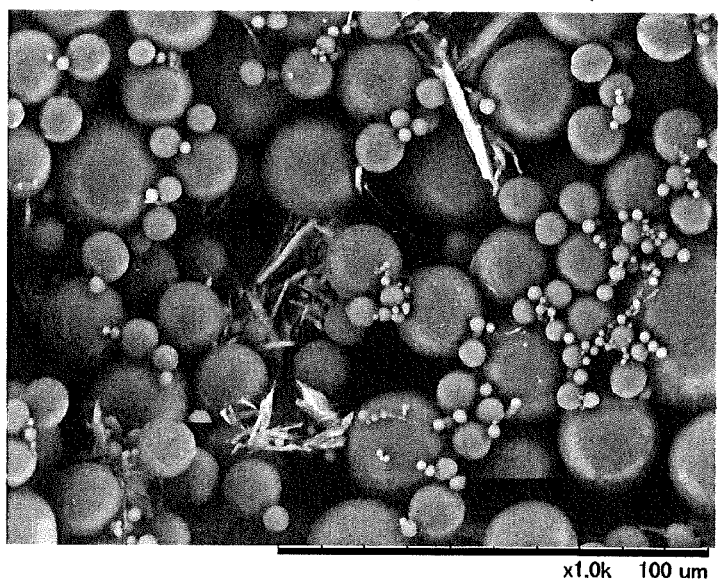
FIG. 11 shows an image-processed SEM photograph of controlled release particles of Comparative Example 4.

On the other hand, as is clear from FIG. 9 to FIG. 11, with the controlled release particles of Comparative Examples 1, 2, and 4, it can be seen that the encapsulated (stored) antibiotic compound (IPBC) is released outside, and separates out as needle crystals.

3. TEM (Transmission Electron Microscope) Observation

The suspension liquids (suspension formulation) of Examples 2, 3, and 5 and Comparative Examples 1 and 2 were freeze-dried, then dispersed in a bisphenol liquid epoxy resin, and thereafter cured with amine. Then, the cured product was cut with an ultramicrotome to expose its cross section; the cross section was dyed with ruthenium tetroxide, and as necessary, also with osmium tetroxide; the cross section was cut out with an ultramicrotome into extremely thin slices, thereby preparing samples. The prepared samples were observed with a transmission electron microscope (model number "H-7100", manufactured by Hitachi, Ltd.).

FIG. 12 to FIG. 16 show image-processed TEM photographs of Examples 2, 3, and 5, and Comparative Examples 1 and 2. In the figures, the white portion shows a detached portion where the controlled release particles are partially detached from the epoxy resin at the time of preparation of the ultrathinly cut sample.

As is clear from FIG. 12 to FIG. 14, in the controlled release particles of Example 2, 3, and 5, a core-shell structure including a core and a shell covering the core can be seen.

Figure 15:
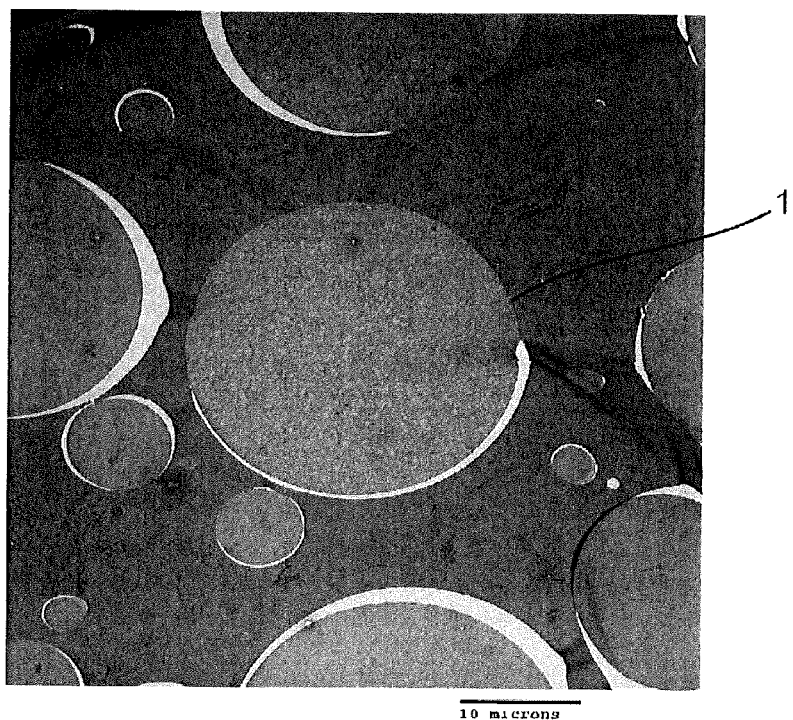
FIG. 15 shows an image-processed TEM photograph of controlled release particles of Comparative Example 1.
Figure 16:
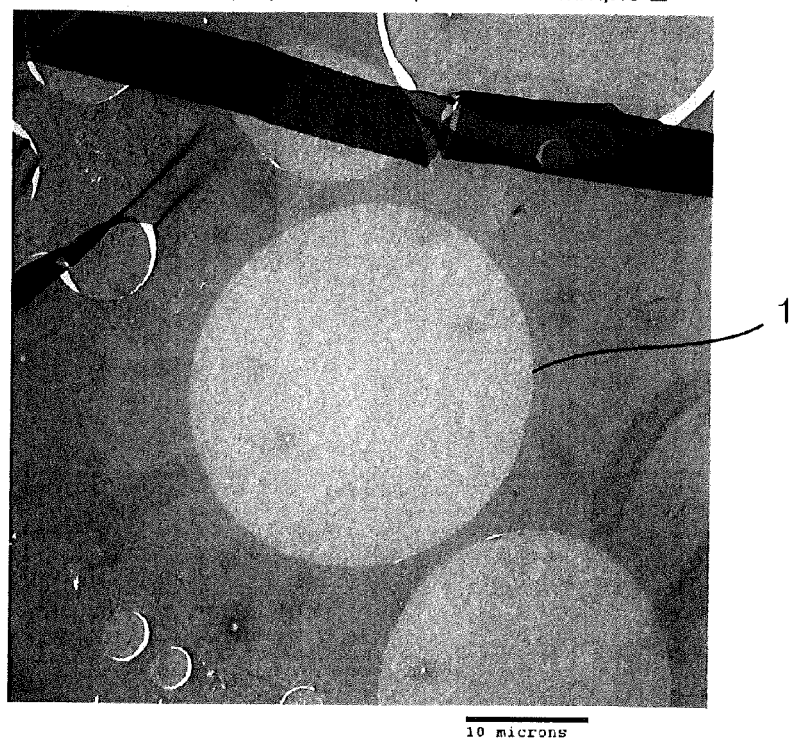
FIG. 16 shows an image-processed TEM photograph of controlled release particles of Comparative Example 2.

On the other hand, as is clear from FIG. 15 and FIG. 16, in the controlled release particles of Comparative Examples 1 and 2, in matrices composed of polyurea produced in interfacial polymerization, polymethyl methacrylate produced by suspension polymerization was dispersed non-homogeneously (island state), and a sea-island structure is seen. That is, in the controlled release particles of Comparative Examples 1 and 2, no core-shell structure is seen.

4. Controlled Release Properties Test (1) Controlled Release Properties Test of IPBC-Containing Controlled Release Particles (Examples 1 to 7 and Comparative Example 4)

Controlled release properties test was conducted for the IPBC-containing controlled release particles of Examples 1 to 7 and Comparative Example 4 in the following manner.

That is, first, the suspension liquids of controlled release particles of Examples 1 to 7 and Comparative Example 4, adjusted to an IPBC concentration of 10 mass % as necessary, were prepared, and the suspension liquid (IPBC concentration 10 mass %) of IPBC in which IPBC was suspended was prepared as a blank.

Then, two sheets of circular filter paper (Toyo Roshi Kaisha, Ltd. No. 5C, corresponds to type 5C of JIS P 3801) were piled and folded to be pleated.

Then, 0.5 mL of the prepared suspension liquids were slowly poured individually onto the filter papers, and thereafter dried in air.

To the filter paper, water in an amount of 1000 mL was passed through using a metered-dose tube pump at a flow rate of 20 mL/hr, and controlled-release rate of the IPBC was calculated using HPLC based on the IPBC amount of the obtained filtrate and the IPBC amount remained in the filter paper. The controlled-release rate in each amount of water passed through was calculated as a cumulative value (that is, total controlled-release rate).

Figure 17:
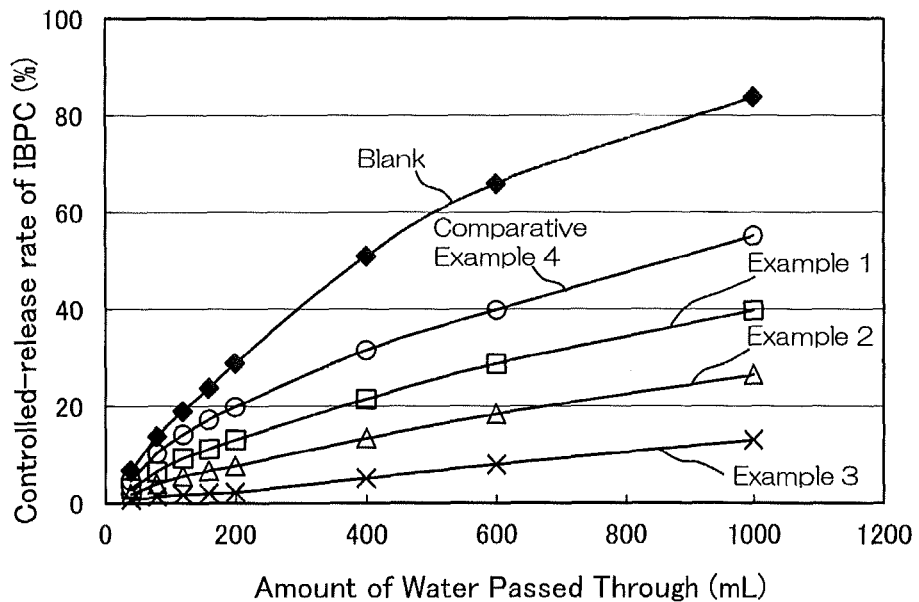
FIG. 17 shows a graph of controlled release properties test of Examples 1 to 3 and Comparative Example 4.
Figure 18:
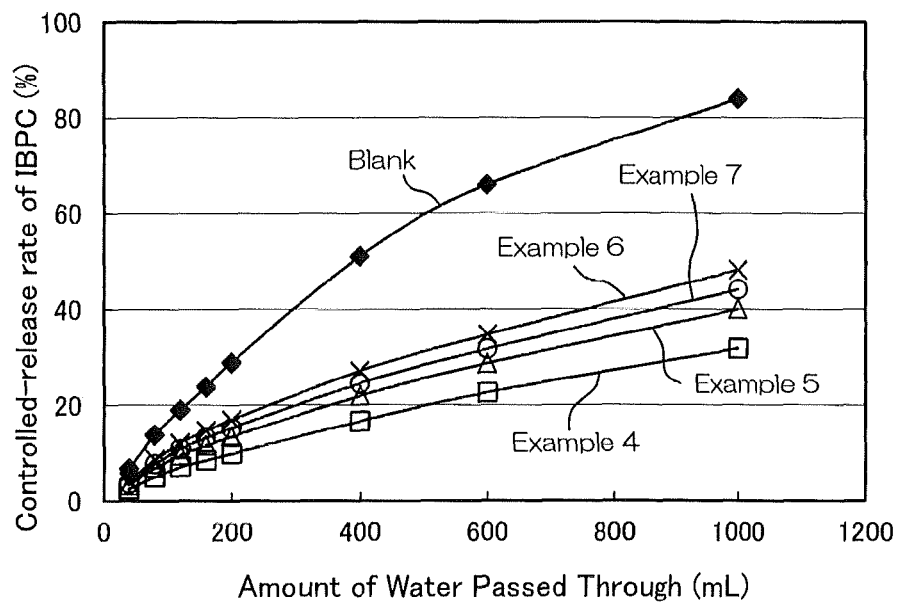
FIG. 18 shows a graph of controlled release properties test of Examples 4 to 7.

The results of Examples 1 to 3, and Comparative Example 4 are shown in FIG. 17, and the results of Examples 4 to 7 are shown in FIG. 18.

(2) Controlled Release Properties Test of OIT-Containing Controlled Release Particles (Example 8 and Comparative Examples 3 and 5)

Controlled release properties test was conducted for the OIT-containing controlled release particles of Example 8 and Comparative Example 3 and 5 in the following manner.

First, suspension liquids (suspension formulation) of controlled release particles obtained in Example 8 and Comparative Examples 3 and 5 were added to a commercially available white acrylic silicone emulsion coating, and OIT, as a blank, was also added thereto so that their OIT concentration was all 0.2 mass %. Thereafter, the coating to which the suspension liquid of the controlled release particles was added was diluted with the ion-exchange water to 1.5 times.

Then, a filter paper (Toyo Roshi Kaisha, Ltd. No. 2, corresponding to type 2 of JIS P 3801) was cut out to a size of 3.5 cm ×3.5 cm and weighed, and impregnated with the above-described paint.

Thereafter, the filter paper was put into a glass bottle, and 15 mL of ion-exchange water was added thereto, and shaken at 40° C. for 18 hours. Then, the ion-exchange water was collected, and 15 mL of ion-exchange water was newly added, and shaken at 40° C. for 18 hours. Thereafter, the above-described ion-exchange water exchange operation was repeated twice.

Controlled-release rate of OIT was calculated using HPLC based on the OIT amount in each of the collected ion-exchange water as described above. The controlled-release rate in the each collected ion-exchange water was calculated as a cumulative value (that is, total controlled-release rate).

Figure 19:
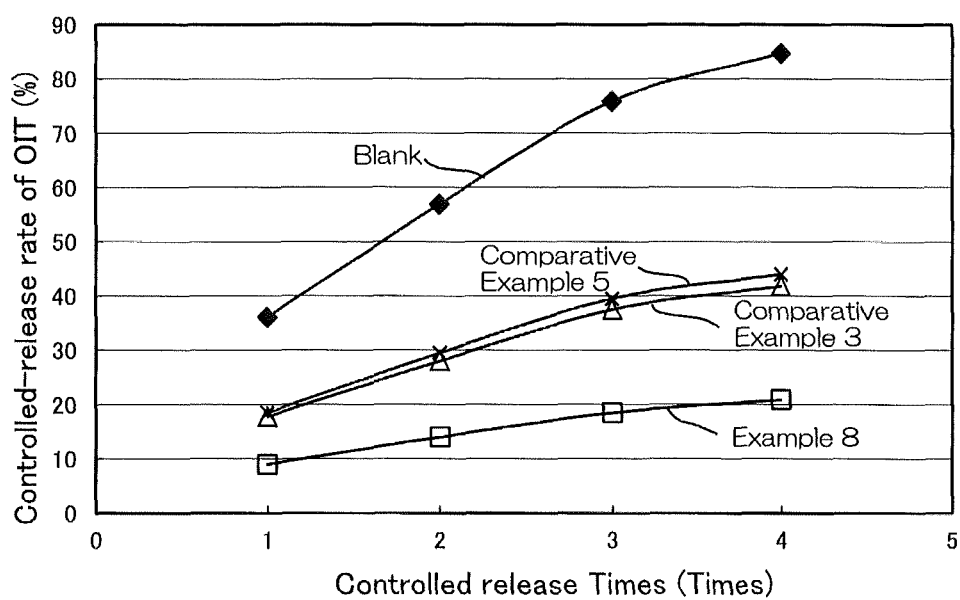
FIG. 19 shows a graph of controlled release properties test of Example 8 and Comparative Examples 3 and 5.

The results of Example 8 and Comparative Examples 3 and 5 are shown in FIG. 19.

(3) Controlled Release Properties Test of IPBC-containing Controlled Release Particles (Example 9 and Comparative Example 6)

Controlled release properties test was conducted for the IPBC-containing controlled release particles in the following manner.

First, suspension liquids of controlled release particles of Example 9 and Comparative Example 6 were prepared in amounts such that their IPBC contents were 100 mg.

Then, a cylindrical filter paper (Toyo Roshi Kaisha, Ltd. No. 84, external diameter×internal diameter×height=28×25×100 mm) was cut transversely, thereby preparing a cylindrical filter paper (three sheets) with a height of 30 mm.

Then, the prepared suspension liquids were slowly poured individually onto two sheets of the filter papers prepared, and thereafter dried in air.

To the remaining one filter paper 1, 100 mg of IPBC as a blank was weighed at the bottom of the filter paper.

To the filter paper, water in an amount of 1000 mL was passed through using a metered-dose tube pump at a flow rate of 20 mL/hr, and controlled-release rate of IPBC was calculated using HPLC based on the IPBC amount of the obtained filtrate. The controlled-release rate in each amount of water passed through was calculated as a cumulative value (that is, total controlled-release rate).

Figure 20:
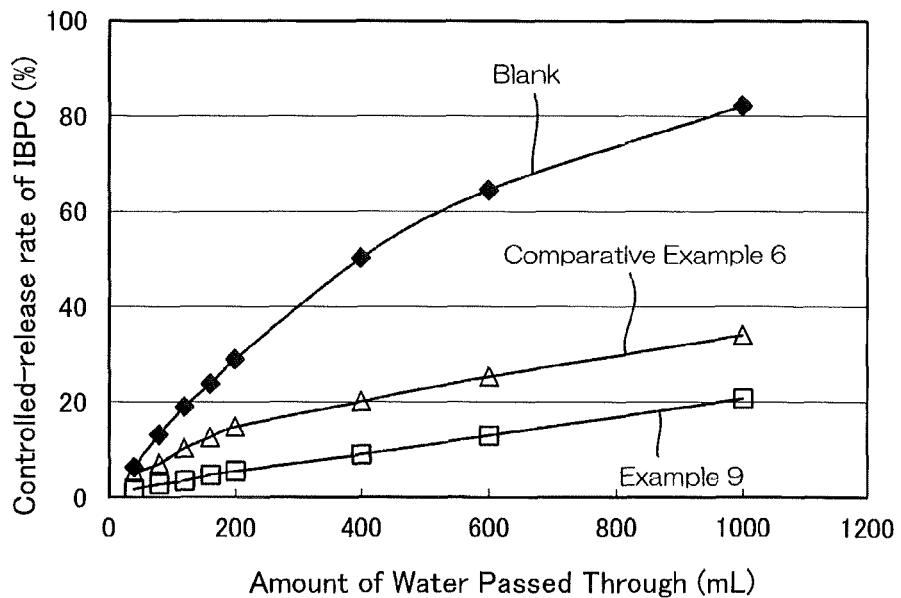
FIG. 20 shows a graph of controlled release properties test of Example 9 and Comparative Example 6.

The results of Example 9 and Comparative Example 6 are shown in FIG. 20.

(4) Controlled Release Properties Test of OIT-Containing Controlled Release Particles (Example 10 and Comparative Example 7)

The controlled-release rate of OIT was calculated in the same manner as in the above-described "(3) controlled release properties test of IPBC-containing controlled release particles" except that instead of the IPBC-containing controlled release particles of Example 9 and Comparative Example 6, the OIT-containing controlled release particles of Example 10 and Comparative Example 7 were used and the controlled-release rate was measured setting OIT as the controlled-release target.

Figure 21:
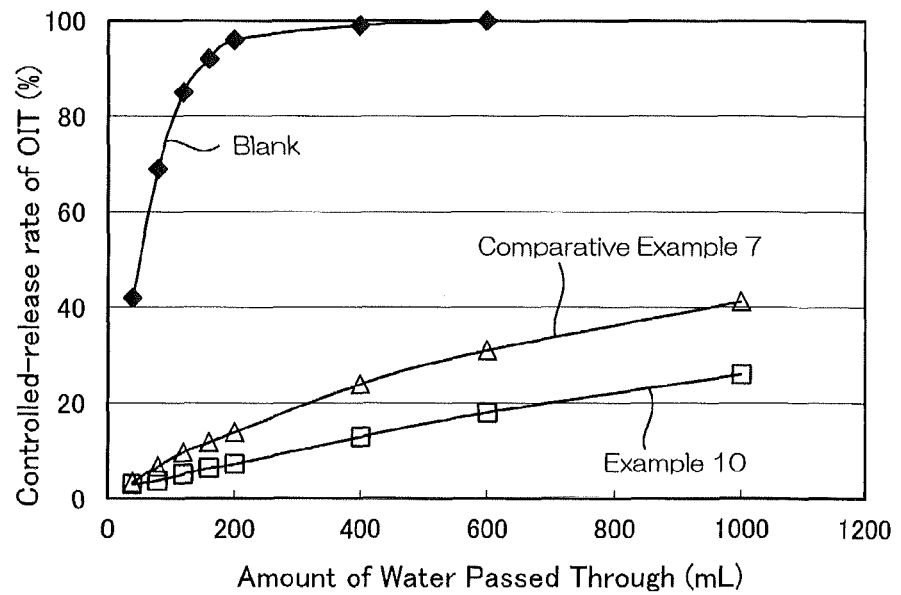
FIG. 21 shows a graph of controlled release properties test of Example 10 and Comparative Example 7.

The results of Example 10 and Comparative Example 7 are shown in FIG. 21.

(5) Controlled Release Properties Test of Propiconazole-Containing Controlled Release Particles The controlled-release rate of Propiconazole was calculated in the same manner as in the above-described "(3) Controlled Release Properties Test of IPBC-containing controlled release particles", except that instead of the IPBC-containing controlled release particles of Example 9 and Comparative Example 6, the Propiconazole-containing controlled release particles of Example 11 and Comparative Example 8 were used, and the controlled-release rate was measured setting Propiconazole as the controlled-release target.

Figure 22:
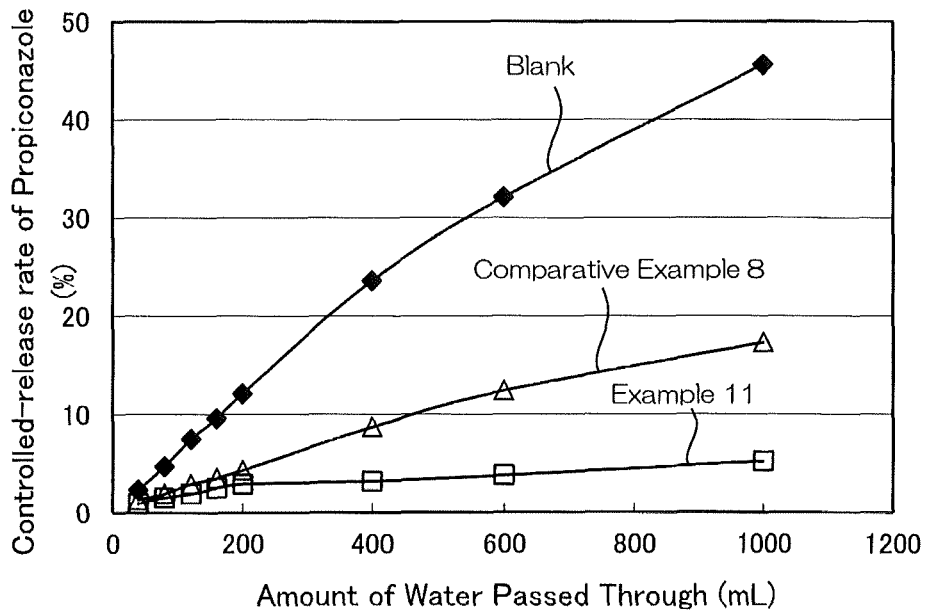
FIG. 22 shows a graph of controlled release properties test of Example 11 and Comparative Example 8.

The results of Example 11 and Comparative Example 8 are shown in FIG. 22.

(6) Controlled Release Properties Test of Flusilazole-Containing Controlled Release Particles of (Example 12 and Comparative Example 9)

The controlled-release rate of Flusilazole was calculated in the same manner as in the above-described "(3) controlled release properties test of IPBC-containing controlled release particles", except that instead of the IPBC-containing controlled release particles of Example 9 and Comparative Example 6, the Flusilazole-containing controlled release particles of Example 13 and Comparative Example 9 were used, and the controlled-release rate was measured setting Flusilazole as the controlled-release target.

Figure 23:
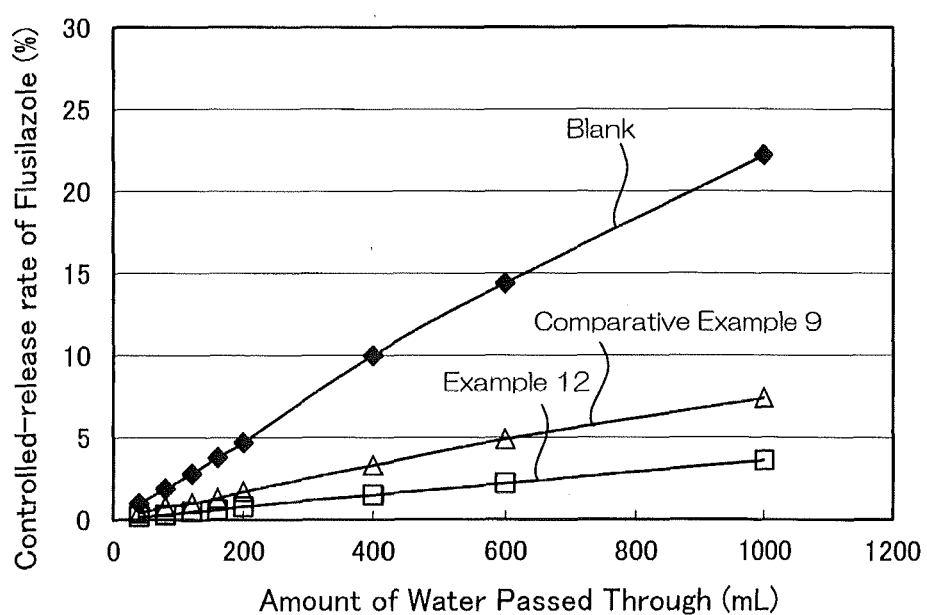
FIG. 23 shows a graph of controlled release properties test of Example 12 and Comparative Example 9.

The results of Example 12 and Comparative Example 9 are shown in FIG. 23.

(7) Controlled Release Properties Test of Prochloraz-Containing Controlled Release Particles (Example 13 and Comparative Example 10)

The controlled-release rate of prochloraz was calculated in the same manner as in the above-described "(3) Controlled Release Properties Test of IPBC-containing Controlled Release Particles", except that instead of the IPBC-containing controlled release particles of Example 9 and Comparative Example 6, the prochloraz-containing controlled release particles of Example 13 and Comparative Example 10 were used, and the controlled-release rate was measured setting the prochloraz as the controlled-release target.

Figure 24:
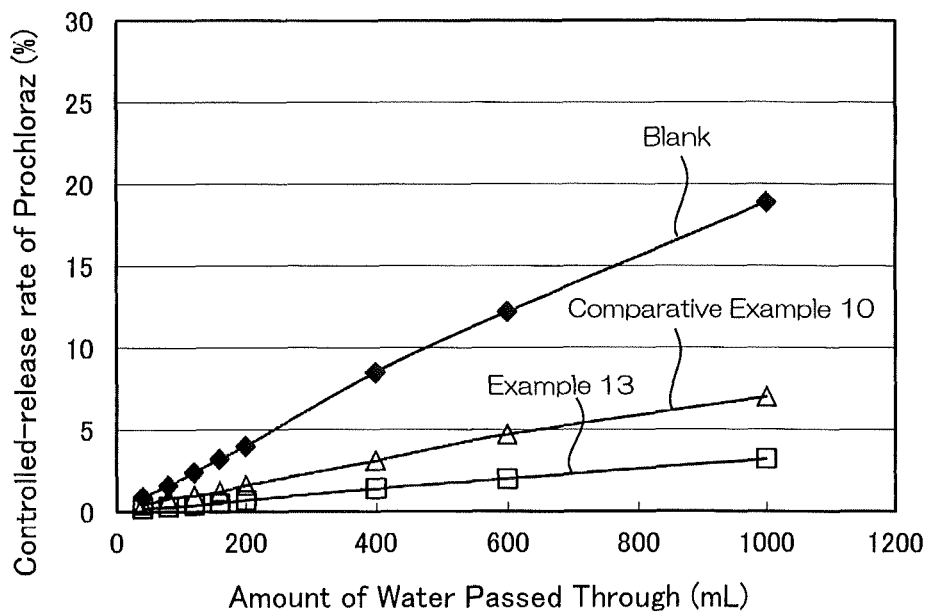
FIG. 24 shows a graph of controlled release properties test of Example 13 and Comparative Example 10.

The results of Example 13 and Comparative Example 10 are shown in FIG. 24.

(8) Controlled Release Properties Test of Cyfluthrin-Containing Controlled Release Particles (Example 14 and Comparative Example 11)

Controlled release properties test was conducted for the cyfluthrin-containing controlled release particles of Example 14 and Comparative Example 11 in the following manner.

First, suspension liquids of controlled release particles of Example 14 and Comparative Example 11 containing 100 mg of cyfluthrin, and 1 g of a solution of 10Mass % cyfluthrin in acetonitrile was prepared as a blank.

Then, two sheets of circular filter paper (Toyo Roshi Kaisha, Ltd. No. 5C, corresponds to type 5C of JIS P 3801) were piled and folded to be pleated.

Then, to the filter paper, the prepared suspension liquids, and the solution of acetonitrile containing cyfluthrin as a black were poured slowly, and thereafter dried in air.

Thereafter, the filter paper was put into a glass bottle, and 180 mL of ion-exchange water/methanol (=50/50 (volume ratio)) mixture liquid was added thereto, and allowed to stand and to be impregnated at room temperature for 24 hours. Then, the ion-exchange water/methanol mixture was collected, 180 mL of another ion-exchange water/methanol mixture liquid was added thereto, and allowed to stand and to be impregnated for 24 hours at room temperature. Thereafter, the above-described ion-exchange water/methanol mixture liquid exchange operation was repeated three times.

The controlled-release rate of the cyfluthrin was calculated using GC based on the ion-exchange water/methanol mixture liquid collected for each time. The controlled-release rate in each time was calculated as a cumulative value (that is, total controlled-release rate).

Figure 25:
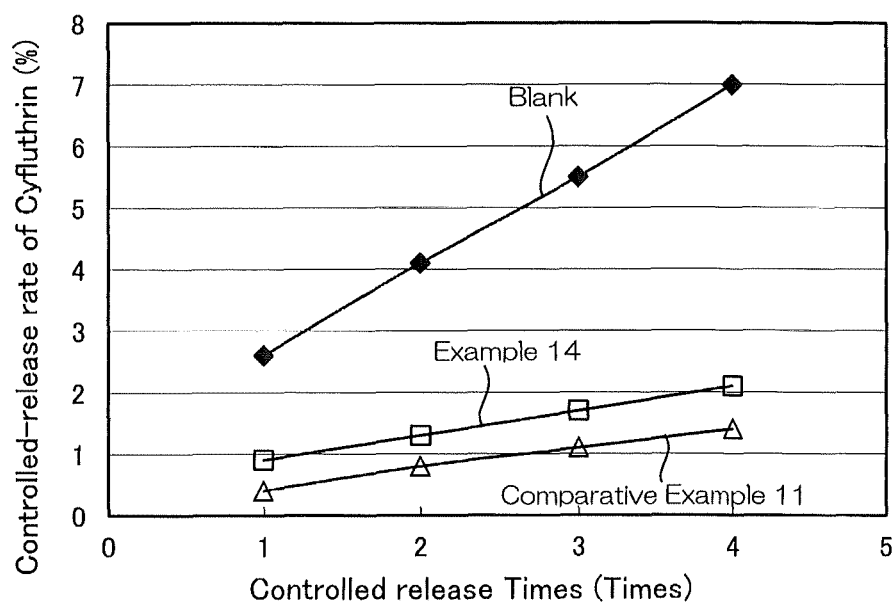
FIG. 25 shows a graph of controlled release properties test of Example 14 and Comparative Example 11.

The results of Example 14 and Comparative Example 11 are shown in FIG. 25.

While the illustrative embodiments of the present invention are provided in the above description, such is for illustrative purpose only and it is not to be construed as limiting the scope of the present invention. Modification and variation of the present invention that will be obvious to those skilled in the art is to be covered by the following claims.

Industrial Applicability

Controlled release particles of the present invention can be applied (or blended) to various industrial products, for example, can be blended in indoor/outdoor paint, rubber, fiber, resin, plastic, adhesive, joint mixture, sealing agent, building material, caulking agent, soil treating agent, lumber, white water in paper-making processes, pigment, treatment liquid for printing plates, cooling water, ink, cutting oil, cosmetic products, nonwoven fabric, spinning oil, leather; and allows controlled-release of the antibiotic compound that is contained in the controlled release particles to exhibit lasting effects of the antibiotic compound.

The invention claimed is:

1. A controlled release particle comprising a core containing an antibiotic compound and a shell covering the core, wherein the controlled release particle is obtained by a production method including
a first step in which a first component containing the antibiotic compound and a polymerizable vinyl monomer is subjected to suspension polymerization to form the core containing the antibiotic compound and a polymer of the polymerizable vinyl monomer, and
a second step in which a second component containing a shell-forming component is subjected to interfacial polymerization to form the shell,
wherein in the second step, the interfacial polymerization is started simultaneously with the start of the suspension polymerization of the first step, or started after the start of the suspension polymerization of the first step, and
wherein the antibiotic compound has a polar term $\delta_{p,compound}$ of 2 to $8[(J/cm^3)^{1/2}]$ and a hydrogen bonding term $\delta_{h,compound}$ of 5.5 to $9.5[(J/cm^3)^{1/2}]$ of a solubility parameter $\delta$, and
the polymer has a polar term $\delta_{p,polymer}$ of 5 to $7[(J/cm^3)^{1/2}]$ and a hydrogen bonding term $\delta_{h,polymer}$ of 8 to $10[(J/cm^3)^{1/2}]$ of the solubility parameter $\delta$, the solubility parameter $\delta$ being defined by Hansen and calculated by van Krevelen and Hoftyzer method.

2. A method for producing a controlled release particle, the method including
a first step in which a first component containing an antibiotic compound and a polymerizable vinyl monomer is subjected to suspension polymerization to form a core containing the antibiotic compound and a polymer of the polymerizable vinyl monomer, and
a second step in which a second component containing a shell-forming component is subjected to interfacial polymerization to form a shell covering the core,
wherein in the second step, the interfacial polymerization is started simultaneously with the start of the suspension polymerization of the first step, or started after the start of the suspension polymerization of the first step.

* * * * *